US010213465B1

(12) United States Patent
Speight et al.

(10) Patent No.: US 10,213,465 B1
(45) Date of Patent: Feb. 26, 2019

(54) METHOD AND SYSTEM FOR REPAIRING DAMAGED TISSUE USING NUCLEATED PLASMA PARTICLES (NUC-P2S) AND MESODERMAL STEM CELLS (MESOSCS)

(71) Applicant: Dragonfly Foundation for Research & Development Corp., Macon, GA (US)

(72) Inventors: Mark O'Neal Speight, Matthews, NC (US); Henry Edward Young, Macon, GA (US)

( * ) Notice: Subject to any disclaimer, the term of this patent is extended or adjusted under 35 U.S.C. 154(b) by 0 days.

(21) Appl. No.: 15/673,899

(22) Filed: Aug. 10, 2017

(51) Int. Cl.
*A61K 35/28* (2015.01)
*A61K 35/545* (2015.01)
*A61M 5/14* (2006.01)

(52) U.S. Cl.
CPC ......... *A61K 35/545* (2013.01); *A61M 5/1411* (2013.01)

(58) Field of Classification Search
CPC .... A61M 5/14; A61M 5/1407; A61M 5/1408; A61K 35/16; A61K 35/28
See application file for complete search history.

(56) References Cited

U.S. PATENT DOCUMENTS

| | | | |
|---|---|---|---|
| 71,357 A | 11/1867 | Barron | |
| 8,034,328 B2 | 10/2011 | Jensen et al. | |
| 2014/0341863 A1* | 11/2014 | Marasco | C12N 5/0663 424/93.7 |
| 2015/0086514 A1* | 3/2015 | Huang | A61K 35/51 424/93.7 |

FOREIGN PATENT DOCUMENTS

| | | |
|---|---|---|
| AU | 201181 A1 | 3/2014 |
| WO | WO-067038 A1 | 5/2013 |

OTHER PUBLICATIONS

Bhartiya, D et al "Very samll embryonic-like stem cells are involved in regeneration of mouse pancreas post-pancreatectomy" Stem Cell Research & Therapy. 2014. 5:106; fig. 5; p. 6, col. 1, lines 2-7.*
M Singer, C Sidwell, GF Long, KC Hawkins, JA Collins, D Hixson, AC Black, Jr, HE Young. Pluripotent and Totipotent Stem Cells in the Pancreas of the Adult Rat. (Poster) Georgia Chapter of the American College of Physicians Scientific Meeting, Savannah Georgia, Mar. 9-11, 2007.
C Sidwell, J Rowell, GF Long, M Singer, KC Hawkins, JA Collins, D Hixson, AC Black, Jr, HE Young. Pluripotent and Totipotent Stem Cells in the Mid-Brain of the Adult Rat. (Poster) Georgia Chapter of the American College of Physicians Scientific Meeting, Savannah Georgia, Mar. 9-11, 2007.
DW Ashley, C Stout, JH Morgan III, GF Long, JA Collins, F Lochner, G McCommon, O Samples, AC Black, Jr, HE Young. Totipotent Stem Cells are Mobilized from Skeletal Muscle into the Circulation of Adult Pigs after Trauma. (Poster) Keystone Symposia on Tissue Engineering and Developmental Biology, Snowbird Utah, Apr. 13, 2007.

(Continued)

*Primary Examiner* — Laura Bouchelle
(74) *Attorney, Agent, or Firm* — Shawn Dansby; Smith Brandenbupe Ltd.

(57) ABSTRACT

The current invention is a method and system for optimally isolating adult derived stem cells from whole blood and reintroducing the adult derived stem cells into a subject at specific target areas having damaged tissue to be repaired.

6 Claims, 7 Drawing Sheets

(56) References Cited

OTHER PUBLICATIONS

L Harris, NM Walsh, GF Long, KC Hawkins, JA Collins, D Hixson, AC Black, Jr, HE Young. Pluripotent and Totipotent Stem Cells in the Kidney of the Adult Rat. (Poster) Keystone Symposia on Tissue Engineering and Developmental Biology, Snowbird Utah, Apr. 14, 2007.

KC Hawkins, Walsh N, GF Long, NL Henson, C Alena, MBL Cole, J Spivey, S Ellis, JA Collins, WJ Butler, Sohnen H, Kross PE, D Hixson, AC Black Jr, HE Young. Discovery of Pluripotent and Totipotent Stem Cells in the Testis of the Adult Rat. Keystone Symposia on Tissue Engineering and Developmental Biology, (Poster) Snowbird Utah, Apr. 14, 2007.

F Lochner, G McCommon, O Samples, JH Morgan III, GE Long, JA Collins, AC Black Jr, HE Young. Native pancreatic islets cultured with decellularized pancreatic matrices, derrived from adult rats show enhancement of insulin synthesis and secretion in response to a glucose challenge. (Poster) Keystone Symposia on Tissue Engineering and Developmental Biology, Snowbird Utah, Apr. 14, 2007.

GF Long, JA Collins, AC Black Jr , HE Young. Native pancreatic islets co-cultured with totipotent stem cells derived from adult rats demonstrate enhancement of insulin synthesis and secretion in response to a glucose challenge. (Poster)Keystone Symposia on Tissue Engineering and Developmental Biology, Snowbird Utah, Apr. 14, 2007.

J McAbee, GF Long, KC Hawkins, JA Collins, D Hixson, AC Black, Jr, HE Young. Pluripotent and Totipotent Stem Cells in the Lung of the Adult Rat. (Poster) Keystone Symposia on Tissue Engineering and Developmental Biology, Snowbird Utah, Apr. 14, 2007.

G McCommon, F Lochner, O Samples, GF Long, JA Collins, AC Black Jr, HE Young. Totipotent stem cells are present in the blood of adult equines. (Poster) Keystone Symposia on Tissue Engineering and Development Biology, Snowbird Utah, Apr. 14, 2007.

AM Rice, L Powell, AJ Thompson, K Detmer, KC Hawkins, GF Long, C Alena, JA Collins, D Hixson, AC Black Jr, HE Young. Pluripotent Stem Cells and Totipotent Stem Cells are Present in the Bone Marrow of the Adult Rat. (Poster)Keystone Symposia on Tissue Engineering and Developmental Biology, Snowbird Utah, Apr. 15, 2007.

C Sidwell, J Rowell, GF Long, M Singer, KC Hawkins, JA Collins, D Hixson, AC Black, Jr, HE Young. Pluripotent and Totipotent Stem Cells in the Brain of the Adult Rat. (Poster) . Keystone Symposia on Tissue Engineering and Developmental Biology, Snowbird Utah, Apr. 12-17, 2007.

M Singer, C Sidwell, GF Long, KC Hawkins, JA Collins, D Hixson, AC Black, Jr, HE Young. Pluripotent and Totipotent Stem Cells in the Pancreas of the Adult Rat. (Poster) Keystone Symposia on Tissue Engineering and Developmental Biology, Snowbird Utah, Apr. 15, 2007.

C Stout, J McKenzie, M McLeod , DW Ashley, GF Long, KC Hawkins, Walsh N, JA Collins, D Hixson, AC Black, Jr, HE Young. Pluripotent and Totipotent Stem Cells in the Heart of the Adult Rat. (Poster)Keystone Symposia on Tissue Engineering and Developmental Biology, Snowbird Utah, Apr. 15, 2007.

NM Walsh, KC Hawkins, GF Long, C Alena, V Krishna, JA Collins, D Hixson, AC Black Jr, HE Young. Discovery of Pluripotent and Totipotent Stem Cells in the Uterine Tubes of the Adult Rat. (Poster)Keystone Symposia on Tissue Engineering and Developmental Biology, Snowbird Utah, Apr. 15, 2007.

HE Young, NL Henson, GF Long, KC Hawkins, Walsh N, C Alena, V Krishna, JA Collins, D Hixson, AC Black, Jr. Location and Characterization of Totipotent and Pluripotent Stem Cells in the Skeletal Muscle of the Adult Rat. (Poster)Keystone Symposia on Tissue Engineering and Developmental Biology, Snowbird Utah, Apr. 15, 2007.

M Barton, J McAbee, K-N Kumar, GF Long, C Alena, V Krishna, MN Woodall, KC Hawkins, JA Collins, D Hixson, FP Bowyer III; AC Black Jr, HE Young. Regeneration of a Broncho-Segment in an Adult Rat Lung via Primitive Stem Cells. (Poster) Keystone Symposium on Tumor Suppressors and Stem Cell Biology, Feb. 24-29, 2008, Vancouver, BC.

E Clarke, R. Abdullah, K Lam, M Twedt, GF Long, C Alena, V Krishna, MN Woodall, KC Hawkins, JA Collins, D Hixson, FP Bowyer III; AC Black Jr, HE Young. CEA-CAM-1 Positive Stem Cells from the Brain of the Adult Rat. (Poster) Keystone Symposium on Tumor Suppressors and Stem Cell Biology, Feb. 24-29, 2008, Vancouver, BC.

J Enclard, S Holwerda, JI Limnios, F Lochner, G McCommon, O Samples, GF Long, C Alena, V Krishna, MN Woodall, JA Collins, KC Hawkins, D Hixson, FP Bowyer III, AC Black Jr, HE Young. Variation in Primitive Stem Cell Numbers in the Adult Porcine and Adult Rat Spleens. (Poster) Keystone Symposium on Tumor Suppressors and Stem Cell Biology, Feb. 24-29, 2008, Vancouver, BC.

J Glow, S Kunze, Charles Kemp, A Brown, GF Long, C Alena, V Krishna, MN Woodall, KC Hawkins, JA Collins, D Hixson, FP Bowyer III; AC Black Jr, HE Young. Maintance and Repair of the Pancreas of the Adult Rat by Primitive Cells. (Poster) Keystone Symposium on Tumor Suppressors and Stem Cell Biology, Feb. 24-29, 2008, Vancouver, BC.

AC Black Jr, HE Young. Primitive Stem Cells in the Dermis and Fat of the Adult Pig. (Poster) Keystone Symposium on Tumor Suppressors and Stem Cell Biology, Feb. 24-29, 2008, Vancouver, BC.

B Kimbrell, A Roberts, F. Lochner, G. McCommon, O. Samples, G.F. Long, C Alena, V Krishna, MN Woodall, JA Collins, KC Hawkins, D Hixson, FP Bowyer III, AC Black Jr HE Young. Spontaneous Repair of Interventricular Spetal Myocardium in the Adult Pig by Stem Cells. (Poster) Keystone Symposium on Tumor Suppressors and Stem Cell Biology, Feb. 24-29, 2008, Vancouver, BC.

V Krishna, JI Limnios, J Glow, E Almon, S Fortson, F. Lochner, G. McCommon, O. Samples, G.F. Long, C Alena, MN Woodall, JA Collins, KC Hawkins, D Hixson, FP Bowyer III, AC Black Jr, HE Young. SSEA-4 Positive Stem Cells and CEA-CAM-1 Positive Stem Cells are Present in Adult Porcine Myocardium. (Poster) Keystone Symposium on Tumor Suppressors and Stem Cell Biology, Feb. 24-29, 2008, Vancouver, BC.

K-N Kumar, S Kunze, n. Henson, JI Limnios, K Lam, F. Lochner, G. McCommon, O. Samples, GF Long, C Alena, V Krishna, MN Woodall, JA Collins, KC Hawkins, D Hixson, FP Bowyer III, AC Black Jr, HE Young. Primitive Stem Cells in the Adult Porcine Pancreas. (Poster) Keystone Symposium on Tumor Suppressors and Stem Cell Biology, Feb. 24-29, 2008, Vancouver, BC.

F Lochner, D Lochner, D Lochner, O Samples, P Jones, G McCommon, S Fortson, C Alena, V Krishna, L. McGill, D Hixson, FP Bowyer III, AC Black Jr, HE Young. Primitive Stem Cells in Adult Feline, Canine, Ovine, Caprine, Bovine, and Equine Peripheral Blood. (Poster) Keystone Symposium on Tumor Suppressors and Stem Cell Biology, Feb. 24-29, 2008, Vancouver, BC.

A Martin, S Fortson, F Lochner, D Lochner, D Lochner, D Hixson, FP Bowyer III; AC Black Jr, HE Young. Primitive Stem Cells in Human Peripheral Blood. (Poster) Keystone Symposium on Tumor Suppressors and Stem Cell Biology, Feb. 24-29, 2008, Vancouver, BC.

Hixson, FP Bowyer III; AC Black Jr., HE Young. Increase in Primitive Stem Cell Numbers in Equine Peripheral Blood Following Stress. (Poster) Keystone Symposium on Tumor Suppressors and Stem Cell Biology, Feb. 24-29, 2008, Vancouver, BC.

HE Young, GF Long, JI Limnios, JA Collins, F Lochner, G McCommon, O Samples, C Alena, V Krishna, D Hixson, FP Bowyer III, AC Black Jr. Decellularized native matrices + primitive adult stem cells + donor islets form islet organoids for the treatment of type-I diabetes mellitus. (Poster) Keystone Symposium on Tumor Suppressors and Stem Cell Biology, Feb. 24-29, 2008, Vancouver, BC.

E Clarke, R. Abdullah, K Lam, M Twedt, GF Long, C Alena, V Krishna, MN Woodall, KC Hawkins, JA Collins, D Hixson, FP Bowyer III; AC Black Jr., HE Young. CEA-CAM-1 Positive Stem Cells from the Brain of the Adult Rat. (Poster) American Association of Anatomists, Experimental Biology Meetings, New Orleans, LA, Apr. 2009.

(56) References Cited

OTHER PUBLICATIONS

CL Fenley, M Jones, GF Long, JI Fenley III, JA Collins, AC Black Jr, HE Young. Decellularized native matrices + primitive adult stem cells + donor islets form islet organoids for the treatment of type-I diabetes. (Poster) American Association of Anatomists, Experimental Biology Meetings, New Orleans, LA, Apr. 2009.

JL Fenley III, CL Fenley, M Jones, J Glow, GF Long, JA Collins, D Hixson, FP Bowyer III, AC Black Jr., HE Young. Maintenance and repair of the pancreas of the adult rat by primitive stem cells. (Poster) American Association of Anatomists, Experimental Biology Meetings, New Orleans, LA, Apr. 2009.

TI Katner, CL Fenley, GF Long, F Lochner, G McCommon, KC Hawkins, D Hixson, FP Bowyer III, AC Black Jr., HE Young. CEA-CAM-1 positive stem cells from the brain of the adult pig. American Association of Anatomists Experimental Biology Meetings, New Orleans, LA, Apr. 2009.

Bhartiya, D., Mundekar, A. Mahale, V., Patel, H. Very small embryonic-like stem cells are involved in regeneration of mouse pancreas post-pancreatectomy Stem Cell Reasearch & Therapy 2014, 5:106, http://stemcellres.com/content/5/5/106.

Bickford, PC, Tan, J, Shytle, RD, Sandberg, CD, EL-Badri, N, Sandberg, PR, Nutraceuticals Synergistically Promote Proliferation of Human Stem Cells Stem Cells and Development 15:118-123 (2006).

Drapeau C; Antarr D; MA H; Yang Z; Tang L; Hoffman RM; Schaeffer DJ; (2010) Mobilization of bone marrow stem cells with StemEnhance® improves muscle regeneration in cardiotoxin-induced muscle injury Cell Cycle, 9:9, 1819-1823, DOI: 10.4161/cc.9.9.11540 http://dx.doi.org/10.4161/cc.9.9.11540.

Kucia M; Reca R; Campbell FR; et al.; A population of very small embryonic-like (VSEL) CX CR4+ SSEA-1+ Oct-4+ stem cells identified in adult bone marrow, Lukemia (2006) 20, 857-869.

Young HE, Morrison DC, Martin JD, Lucas PA. Cryopreservation of embryonic chick myogenic lineage-committed stem cells. Journal of Tissue Culture Methods, 13:275-284, 1991.

Young, H.E., Sippel, J., Putnam, L.S., Lucas, P.A., Morrison DC.: Enzyme-linked immuno-culture assay. Journal of Tissue Culture Methods, 14:31-36, 1992.

Young HE, Ceballos EM, Smith JC, Lucas PA, Morrison DC. Isolation of embryonic chick myosatellite and pluripotent stem cells. Journal of Tissue Culture Methods, 14:85-92,1992.

Young HE, Ceballos EM, Smith JC, Mancini ML, Wright RP, Ragan BL, Bushell I, Lucas PA. Pluripotent mesenchymal stem cells reside within avian connective tissue matrices. In Vitro Cellular & Developmental Biology, 29A:723-736, 1993.

Pate DW, Southerland SS, Grande DA, Young HE, Lucas PA. Isolation and differentiation of mesenchymal stem cells from rabbit muscle. Surgical Forum, XLIV:587-589,1993.

Rogers JJ, Young HE, Adkison LR, Lucas PA, Black AC Jr. Differentiation factors induce expression of muscle, fat, cartilage, and bone in a clone of mouse pluripotent mesenchymal stem cells. The American Surgeon 61(3):1-6, 1995.

Young HE, Mancini ML, Wright RP, Smith JC, Black AC Jr, Reagan CR, Lucas PA. Mesenchymal stem cells reside within the connective tissues of many organs. Developmental Dynamics 202:137-144, 1995.

Lucas PA, Calcutt AF, Southerland SS, Wilson JA, Harvey RL, Warejcka D, Young HE. A population of cells resident within embryonic and newborn rat skeletal muscle is capable of differentiating into multiple mesodermal phenotypes. Wound Repair and Regeneration 3:449-459, 1995.

Warejcka DJ, Harvey R, Taylor BJ, Young HE, Lucas PA. A population of cells isolated from rat heart capable of differentiating into several mesodermal phenotypes. J. Surg. Res. 62:233-242, 1996.

Dixon K, Murphy RW, Southerland SS, Young HE, Lucas PA. Recombinant human bone morphogenetic proteins-2 and 4 induce several mesenchymal phenotypes in culture. Wound Repair and Regeneration 4:374-380, 1996.

Young HE, Wright RP, Mancini ML, Lucas PA, Reagan CR, Black AC Jr. Bioactive factors affect proliferation and phenotypic expression in progenitor and pluripotent stem cells. Wound Repair and Regeneration 6(1):65-75, 1998.

Young HE; Rogers JJ; Adkison LR; Lucas PA; Black AC Jr; Muscle Morphogenetic Protein Induces Myogenic Gene Expression in Swiss-3T3 Cells. Wound Rep Reg 6(6):543-554, 1998.

Young HE, Steele T, Bray RA, Detmer K, Blake LW, Lucas PA, Black AC Jr. Human pluripotent and progenitor cells display cell surface cluster differentiation markers CD10, CD13, CD56, CD90 and MHC Class-I. Proc. Soc. Exp. Biol. Med. 221:63-71, 1999.

Young HE. Stem cells and tissue engineering. In: Gene Therapy in Orthopaedic and Sports Medicine, J. Huard and F.H. Fu, eds., Springer-Verlag New York, Inc., Chap. 9, p. 143-173, 2000.

Young HE, Duplaa C, Young TM, Floyd JA, Reeves ML, Davis KH, Mancini GJ, Eaton ME, Hill JD, Thomas K, Austin T, Edwards C, Cuzzourt J, Parikh A, Groom J, Hudson J, Black AC Jr Clonogenic analysis reveals reserve stem cells in postnatal mammals. I. Pluripotent mesenchymal stem cells. Anat. Rec. 263:350-360, 2001.

Young HE, Steele T, Bray RA, Hudson J, Floyd JA, Hawkins K, Thomas K, Austin T, Edwards C, Cuzzourt J, Duenzl M, Lucas PA, Black AC Jr. Human reserve pluripotent mesenchymal stem cells are present in the connective tissues of skeletal muscle and dermis derived from fetal, adult, and geriatric donors. Anat. Rec. 264:51-62, 2001.

Romero-Ramos M, Vourc'H P, Young HE, Lucas PA, Wu Y, Chivatakarn O, Zaman R, Dunkelman N, El-Kalay MA, Chesselet M-F Neuronal differentiation of stem cells isolated from adult muscle. J Neurosci Res 69:894-907, 2002.

Young HE. Existence of reserve quiescent stem cells in adults, from amphibians to humans. Curr Top Microbiol Immunol. 280:71-109, 2004.

Young HE, Black Jr AC. Adult stem cells. Anat. Rec. 276A:75-102, 2004.

Young HE, Duplaa C, Romero-Ramos M, et al. Adult Reserve Stem Cells and their Potential for Tissue Engineering. Cell Biochem Biophys, 40(1):1-80, 2004.

Young HE; Duplaa C; Yost MJ; et al. Clonogenic analysis reveals reserve stem cells in postnatal mammals. II. Pluripotent epiblastic-like stem cells. Anat. Rec. 277A:178-203, 2004.

Vourc'H P, Romero-Ramos M, Chivatakarn O, Young HE, et al.; Isolation and characterization of cells with neurogenic potential from adult skeletal muscle. Biochemical and Biophysical Research Communications 317:893-901, 2004.

Seruya M, Shah A, Pedrotty D, DU Laney T, Melgiri R, McKee JA, Young HE, Niklason LE. Clonal Population of adult stem cells: life span and differentiation potential. Cell Transplant 13:93-101, 2004.

Young HE, Black AC Jr. Differentiation potential of adult stem cells. In: Contemporary Endocrinology: Stem Cell in Endocrinlgy, L.B. Lester, ed., The Humana Press Inc., Totowa, NJ. Chap. 4, p. 67-92, 2005b.

Vourc'h P, Lacar B, Mignon L, Lucas PA, Young HE, Chesselet MF. Effect of neurturin on mulitpotent cells isolated from the adult skeletal muscle. Biochem Biophys Res Commun 332:215-223, 2005.

Henson NL, Heaton ML, Holland BH, Hawkins KC, Rawlings B, Eanes E, Bozof R, Powell S, Grau R, Fortney J, Peebles B, Kumar D, Yoon JI, Godby K, Collins JA, Sood R, Hixson D, Bowyer III, FP, Black Jr AC, Young HE. Karyotypic analysis of adult pluripotent stem cells. Histology and Histopathology, 20: 769-784, 2005.

Mignon L, Vourc'h P, Romero-Ramos M, Osztermann P, Young HE, et al.; Transportation of multipotent cells extracted from adult skeletal muscles into the adult subventricular zone of adult rats. J Comp Neurol 491:96-108, 2005.

Young HE, Duplaa C, Katz R, et al.; Adult-derived stem cells and their potential for tissue repair and molecular medicine; J Cell Molec Med 9:753-769, 2005.

Young HE, Black AC Jr. Adult-derived stem cells. Minerva Biotechnologica 17:55-63, 2005.

Stout CL, Ashley DW, Morgan III JH, Long GF; Collins JA, Limnios JI, Lochner F, McCommon G, Hixson D, Black Jr AC, Young HE. Primitive Stem Cells Residing in the Skeletal Muscle of

(56) References Cited

OTHER PUBLICATIONS

Adult Pigs are Mobilized into the Peripheral Blood Following Trauma. American Surgeon 73 (11):1106-1110, 2007.

Stout CL, McKenzie J, Long G, Henson N, Hawkins KC, Ashley OW, Collins J, Hixson D, Black Jr AC, Young HE. Discovery of pluripotent and totipotent stem cells in the heart of the adult rat. Amer Surg 73:S63, 2007.

Young HE and Black Jr AC. Naturally occurring adult pluripotent stem cells. In: Stem Cells: From Biology to Therapy, Advances in Molecular Biology and Medicine. 1st Ed, R.A. Meyers, Ed, Wiley-Blackwell-VCH Verlag GmbH & Co. KGaA. Chap 3, pp. 63-93, 2013. http://onlinelibrary.wiley.com/doi/10.1002/3527600906.mcb.201200017/abstract.

Young HE, Hyer L, Black AC Jr, Robinson JS Jr. Adult stem cells: from bench-top to bedside. In: Tissue Regeneration: Where Nanostructure Meets Biology, 3DBiotech, North Brunswick, NJ Chap 1, pp. 1-60, 2013a.

Young HE, Hyer L, Black AC Jr, Robinson JS Jr. Treating Parkinson disease with adult stem cells. J Neurological Disorders, 2:1, 2013b, http://dx.doi.org/10.4172/jnd.100121.

McCommon GW, Lochner F, Black Jr AC, Young HE. Primitive Stem Cells are Present in the Blood of Adult Equines and Increase with Moderate Exercise or Ingestion of the Cyanobacter, Aphanizomenon Flos-Aquae. Autocoids 2: 103, 2013, doi:10.4172/2161-0479.1000103.

Young HE, Black AC. Pluripotent Stem Cells. Endogenous versus Reprogrammed, a Review. MOJ Orthop Rheumatol 1(4): 00019, 2014. https://lnkd.in/eUYkgU6" MOJ ISSN: 2374-6939MOJOR.

Young HE; Limnios IJ; Lochner F; et al. Pancreatic Islet Composites Secrete Insulin in Response to a Glucose Challenge . J Stem Cell Res. 2017; 1-12.

Young HE; Henson NL; Black GE; et al. Location and Characterization of Endogenous Naturally-Occurring Stem Cells in the Skeletal Muscle of the Adult Rat. J Stem Cell Res. 2017; 1-17.

Young HE; Speight MO; Black AC Jr; et al. Functional Cells, Maintenance Cells, and Healing Cells. J Stem Cell Res. 1(1): 1-4, 2017.

Young HE; Lochner F; Lochner D; et al. Primitive Stem Cells in Adult Feline, Canine, Ovine, Caprine, Bovine, and Equine Peripheral Blood. J Stem Cell Res. 1(1) 004: 1-6, 2017.

* cited by examiner

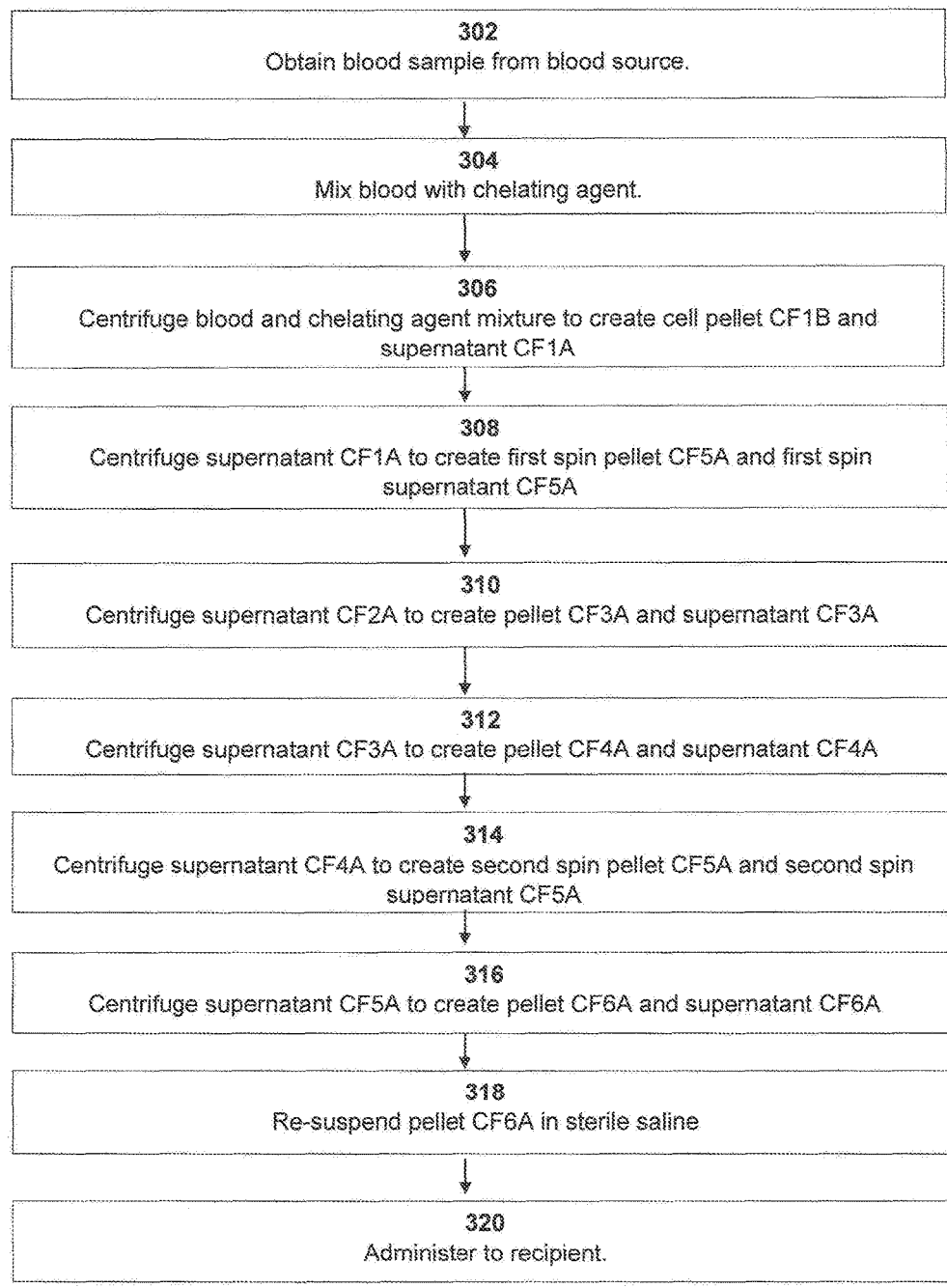

FIG. 2

```
502
Obtain blood sample from blood source.
    ↓
504
Mix blood with chelating agent.
    ↓
506
Centrifuge blood and chelating agent mixture to create cell pellet CF1B and
supernatant CF1A
    ↓
508
Centrifuge supernatant CF1A to create pellet CF2A and supernatant CF2A
    ↓
510
Centrifuge supernatant CF2A to create pellet CF6A and supernatant CF6A
    ↓
512
Re-suspend pellet CF6A in saline to create a composition
    ↓
514
Administer composition of saline-CF6A to recipient by nebulization
```

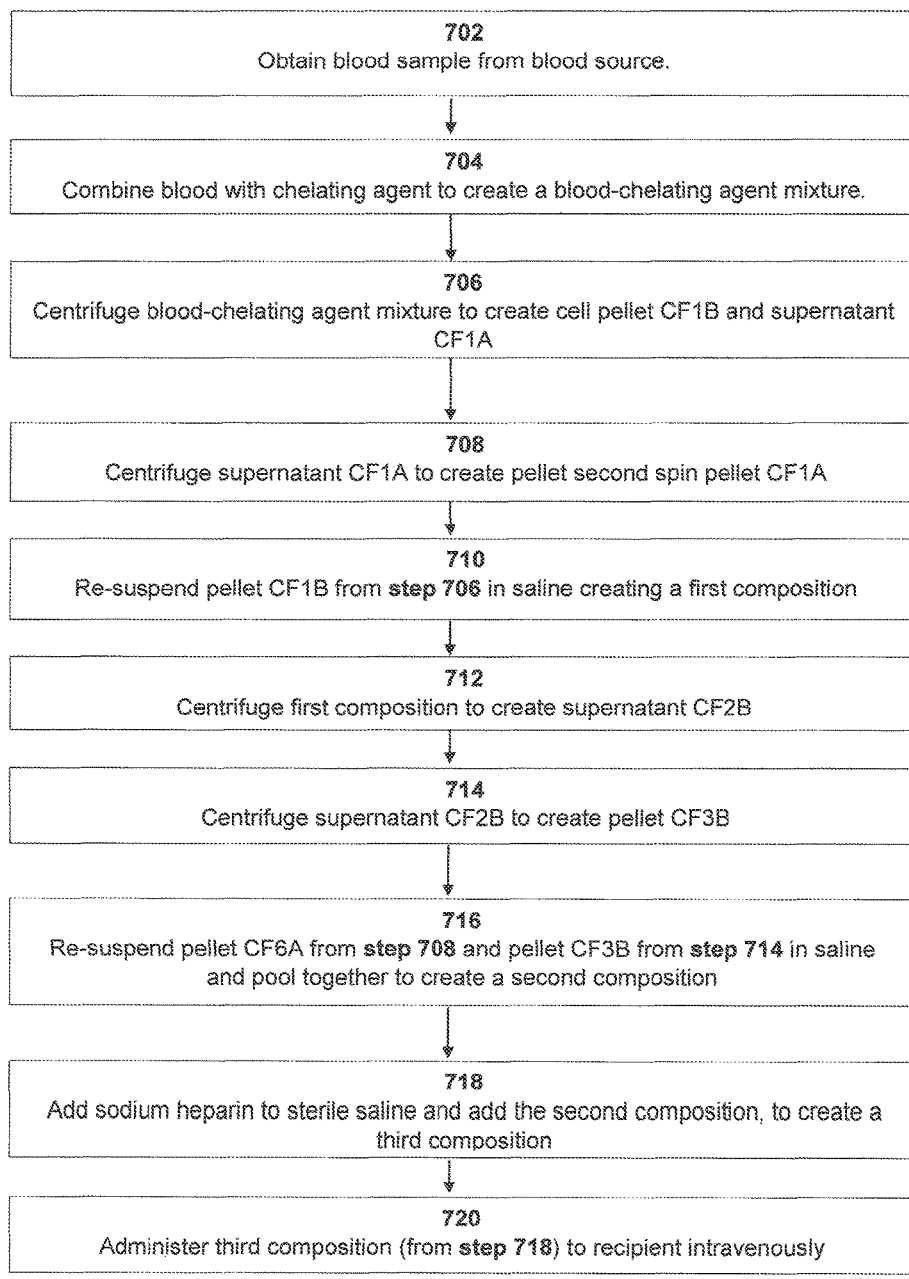

METHOD AND SYSTEM FOR REPAIRING DAMAGED TISSUE USING NUCLEATED PLASMA PARTICLES (NUC-P2S) AND MESODERMAL STEM CELLS (MESOSCS)

TECHNICAL FIELD

The field of the present invention involves the repair of damaged tissue by the isolation and introduction of adult derived stem cells to the damaged tissue.

BACKGROUND

The current methods of isolation include sourcing stem cells from the following; adult bone marrow, adipose tissue, fibroblastic tissues, blood, embryonic tissue. Adult differentiated cells are artificially induced to become more embryonic-like by transferring genetic material into the cells such as, for example, induced pluripotent stem cells (iPSCs). Non-embryonic stem cells are artificially induced to differentiate into the desired tissue by transferring genetic material into these cells. To prevent teratoma formation embryonic stem cells and induced-pluripotent stem cells are encouraged to differentiate using inductive agents either singly or in combination. Adult stem cells are also encouraged to differentiate using inductive agents, either singly or in combination. Induced embryonic, induced pluripotent, and adult stem cells are propagated and then introduced into the damaged tissue, which they then replace. However, such current methods of isolation and introduction of embryonic, iPSC, and adult stem cells have multiple inherent problems.

Embryonic sourcing of stem cells is highly controversial and subject to strict regulation concerning their collection and use. Use of adult derived stem cells engender less controversy and scrutiny, but current methods of obtaining and using them still presents several problems.

Obtaining stem cells from adult differentiated cells require using viruses to transfer embryonic genes into the differentiated cells. These artificially created cells, for example, iPSCs, can form teratomas when placed into adult tissues in an undifferentiated state. In addition, the viruses used for transfer of the genetic material can go "rogue" causing multiple problems within the altered cells. Instances involving transfer of genetic material by viruses for tissue repair are rife with problems such as infections and cancer.

The current invention utilizing mesodermal stem cells (MesoSCs) and nucleated plasma particles (Nuc-P2s) derived from whole blood, circumvents the dangers inherent in using viruses and foreign genetic material. Neither adult MesoSCs nor Nuc-P2s manipulate the genetics of the damaged tissues, but incorporate into the recipient's own healthy tissue where they are introduced.

Currently, the principal methods of obtaining adult stem cells include bone marrow aspiration, liposuction from adipose tissue, enzymatic digestion of solid tissue biopsies, and isolation from blood. The first three methods of adult stem cell collection are problematic because they are invasive and require the use of anesthesia and surgical expertise. They also increase the risk the patient may experience complications and pain from the extraction procedure. Enzymatic digestion of biopsy tissue may leave remnants of tissue proteins and/or enzymes, which may elicit an immune response.

While less expensive, time consuming and invasive, collection of stem cells by the use of venipuncture causes an immediate clotting response, reducing the number of adult stem cells in the sample. Consequently, while existing stem cell isolation from blood is far less expensive and less invasive than other methods currently in use, the yield of stem cells is much lower.

The existing methods of treating damaged tissue with stem cells suffer from problems similar to the problems of stem cell isolation methods. Treatment of damaged central nervous system tissue by stem cells is currently done by a craniotomy, intra-thecal transplant or intra-nasally. A craniotomy adds the risks and expense of neurosurgery. In intra-thecal transplants, the exact volume of cerebral spinal fluid must be returned to the patient or they risk an extended period of severe headaches. Current intra-nasal application requires the use of hyaluronidase or mannitol, which compromises the function of nasal tissue, and risks the patient contracting meningitis. Intravenous introduction of stem cells derived from adipose tissue have the potential to cause death due to a fat embolism and intravenous introduction of stem cells cannot repair damage to the brain and spinal cord due to an inability to pass through the blood-brain barrier. Intravenous introduction of stem cells cannot repair damage to the epithelia lining the lung alveoli due to the gas/liquid basement membrane barrier between the capillaries and alveoli. Furthermore, during intravenous injection of stem cells during treatment, the clotting response reduces the number of adult stem cells reaching the treatment area. Currently, few advances have been made in optimizing the cell's reparative activities and proliferation rates to increase the number of effective stem cells used to treat damaged tissues.

Accordingly, what is needed are alternative methods which increase the numbers and availability of adult MesoSCs and Nuc-P2s in the blood circulation for use in repairing tissue damage via collected MesoSCs and Nuc-P2s separated by size and suitability for specific types of tissue repair, and optimizing the availability of delivered MesoSCs and/or nucleated plasma particles to damaged tissue. The present invention addresses these needs by increasing the available levels of adult MesoSCs and Nuc-P2s and optimizing the conditions for collecting the same. Further, the present invention allows for isolation of the different types of nucleated plasma particles and MesoSCs and their targeted introduction into damaged tissues in a manner that maximizes regeneration of damaged tissues.

DISCLOSURE OF THE INVENTION

The method and system of the subject invention is directed to a more effective method of isolating MesoSCs and Nuc-P2s from blood, and delivering the MesoSCs and Nuc-P2s to damaged tissue, while optimizing the availability of MesoSCs and Nuc-P2s for tissue repair. It should be understood that "damaged tissue" as used herein, refers to tissue that has been damaged due to age or illness or injury or tissue that is receiving medical treatment or medical rejuvenation. In a preferred embodiment of the invention, the methods of stimulating and inducing of the subject invention are beneficial for the optimized collection of adult MesoSCs and Nuc-P2s from blood.

In a preferred embodiment, the subject invention is directed to a method of isolating MesoSCs in a blood sample from the blood pellet after hematocrit formation. In a second preferred embodiment, the subject invention is directed to a method of isolating subtypes of Nuc-P2s and optimizing their delivery and availability to repair damaged tissue. The subtypes of Nuc-P2s identified herein are as follows: Nuc-$P2_{0.1-2.0}$ meaning Nuc-P2s having a size from 0.1 microns to 2.0 microns; Nuc-$P2_{>2,<4}$, meaning Nuc-P2s having a size from greater than 2.0 microns to less than 4.0 microns; Nuc-P2$_{>4-<6}$, meaning Nuc-P2s having a size greater than 4.0 microns to less than 6.0 microns; Nuc-P2$_{6-8}$, meaning Nuc-P2s having a size from 6.0 microns to 8.0 microns; and Nuc-P2$_{>8-<10}$, meaning Nuc-P2s having a size greater than 8.0 microns to less than 10 microns.

Another preferred embodiment of the subject invention is an optimized method of delivering nucleated plasma particles to damaged central nervous system tissues.

Another preferred embodiment of the subject invention is an optimized method of delivering nucleated plasma particles to damaged respiratory system tissue.

Another preferred embodiment of the subject invention is an optimized method of delivering MesoSCs and Nuc-P2s to damaged tissues including, by way of example, but not limited to cardiac tissue, internal organs, internal organ systems and joints systemically.

Another preferred embodiment of the subject invention is an optimized method of delivering MesoSCs and Nuc-P2s directly to the site of damaged tissues including by way of example, but not limited to cardiac tissue, joints, internal organs, internal organ systems, skeletal muscle, kidney tubule cells, liver, pancreas, joints, and smooth muscle tissue of the gut, by way of injection, with or without fluoroscopic, ultrasound or other imaging guidance.

In another preferred embodiment the subject invention is directed to a system for treating damaged tissue in a subject with optimally isolated adult derived MesoSCs and Nuc-P2s.

These and other benefits, advantages, and embodiments of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIG. 1 is an isolation flow chart of MesoSCs and Nuc-P2s from whole blood for the embodiment where the damaged tissue to be treated is central nervous system tissue.

FIG. 2 is an isolation flow chart describing the optimal isolation of MesoSCs and Nuc-P2s from whole blood beginning where the damaged tissue to be treated is respiratory tissue.

FIG. 3 illustrates a preferred embodiment of the invention wherein the damaged tissue to be treated is an internal organ or internal organ system

BEST MODE FOR CARRYING OUT THE INVENTION

Figure 1A:
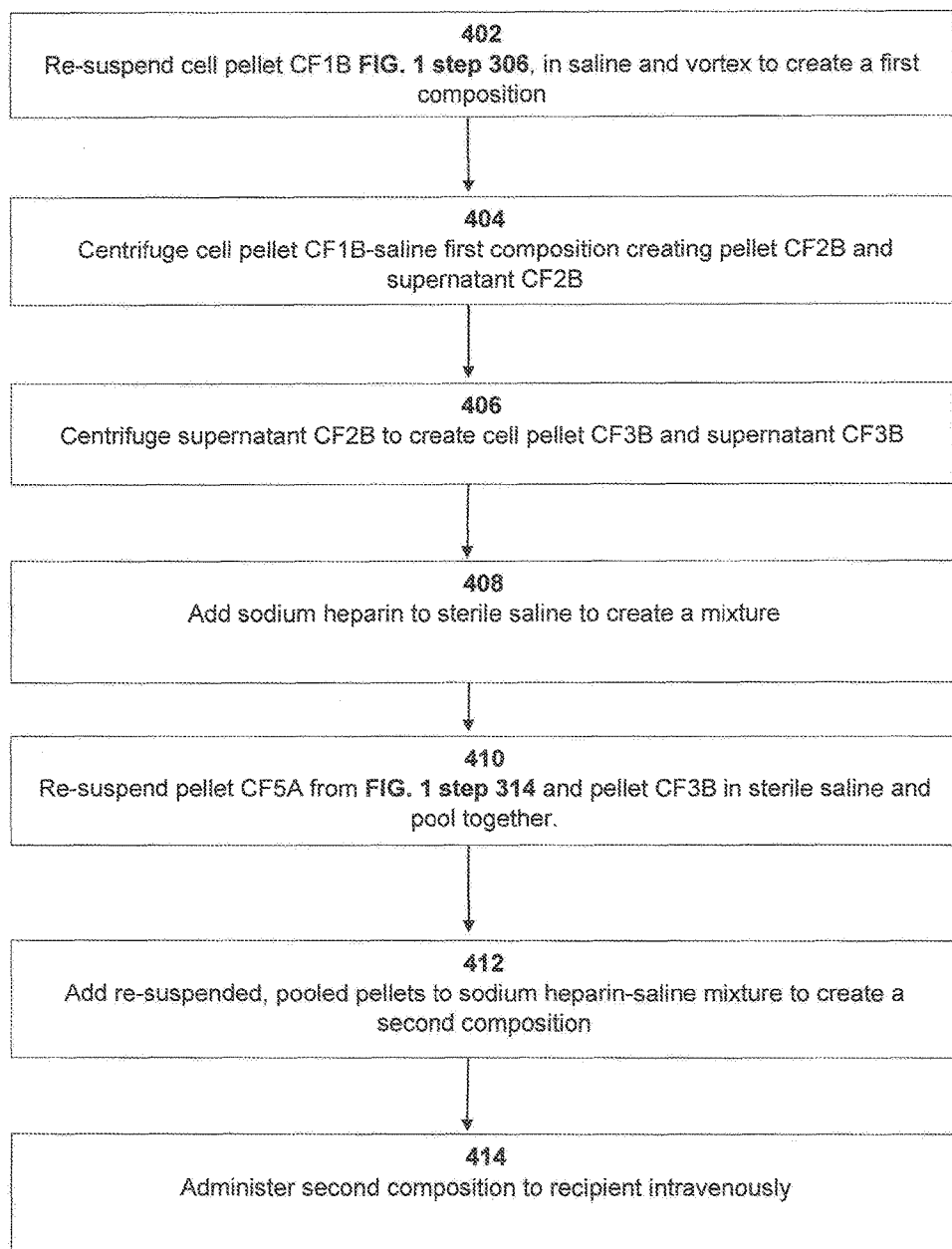
FIG. 1a is a continuation from FIG. 1 of the isolation flow chart of MesoSCs and Nuc-P2s from whole blood where the damaged tissue to be treated is central nervous system tissue, beginning with cell pellet CF1B through MesoSC administration to the recipient by IV drip.

As used herein, the following terms will have these meanings:

Blood source—A human or non-human mammal or non-mammalian animal from which blood is drawn specifically for isolating MesoSCs and Nuc-P2s.

Damaged tissue—This term refers to tissue that has been damaged due to age or illness' or injury or tissue that is receiving medical treatment or medical rejuvenation.

GLSCs—Germ layer lineage stem cells.

MesoSCs—Mesodermal stem cells.

Mobilizer and/or Mobilizing agent αA substance or action that causes MesoSCs and Nuc-P2s located in the connective tissue to migrate into the peripheral vasculature of a blood source. Examples of mobilizers include, but are not limited to Aphanizomenon flos-aquae, chorella, exercise and physical trauma Nuc-P2s—Nucleated plasma particles.

Nuc-P2s$_{>8-<10}$—Nucleated plasma particles having the characteristics of transitional-pluripotent stem cells/germ layer lineage stem cells (Tr-PSCs/GLSCs) and having a size of about greater than 8:0 microns to about less than 10 microns.

Nuc-P2s$_{6-8}$—Nucleated plasma particles having the characteristics of pluripotent stem cells (PSCs) and having a size of about 6.0 microns to about 8.0 microns.

Nuc-P2s>$_{4-<6}$—Nucleated plasma particles having the characteristics of larger transitional-totipotent stem cells/pluripotent stem cells (Tr-TSCs/PSCs) and having a size of about greater than 4.0 microns to about less than 6.0 microns.

Nuc-P2s$_{>2-<4}$—Nucleated plasma particles having characteristics of smaller transitional totipotent stem cell/pluripotent stem cells (Tr-TSC/PSCs) and having a size of about greater than 2.0 microns to about less than 4.0 microns.

Nuc-P2s$_{0.1-2}$—Nucleated plasma particles having the characteristics of totipotent stem cells (TSCs) and having a size of about 0.1 microns to about 2.0 microns.

Pooled, pooling—A collection of multiple samples of the same origin or point in the method, whether blood, plasma, pellet, or supernatant are added together to increase the yield of MesoSCs and/or Nuc-P2s desired. Depending on the treatment, one can pool populations separately, or combine them.

Recipient—A mammal or non-mammal having damaged tissue, which receives MesoSCs and/or Nuc-P2s to repair the damaged tissue.

Stimulator—A substance that prompts Nuc-P2s located in connective tissue to proliferate. Examples of stimulators include, but are not limited to antioxidants and/or flavonoids. Examples of stimulators include but are not limited to fresh, frozen, and powdered blueberries, raspberries, blackberries, and concord grapes.

Although stem cell treatment of damaged tissues has been proven clinically effective, isolating sufficient amounts of stem cells for treatment of damaged tissues has remained time consuming, expensive, invasive and, in the case of embryonic stem cells, controversial. Furthermore, introducing sufficient amounts of stem cells to effectively repair damaged tissues are problematic for the same reasons. Accordingly, the subject invention provides alternative methods and a system that can be used to increase the number of MesoSCs and Nuc-P2s for harvest prior to their isolation and introduction to damaged tissues while reducing the invasiveness, costs and duration of the procedure. Further, the subject invention provides additional methods of obtaining sufficient amounts of MesoSCs and Nuc-P2s from non-P2s from non-embryonic sources thereby reducing the controversy surrounding stem cell treatments.

It was unexpectedly found that utilizing a series of stimulators and mobilizers caused adult (non-embryonic) stem cells to proliferate and migrate into the circulatory system, thereby increasing amounts of adult MesoSCs and Nuc-P2s available for collection from blood. Examination of MesoSCs and Nuc-P2s obtained in this manner unexpectedly revealed that the MesoSCs resided in the cell pellet of the hematocrit, whereas the Nuc-P2s resided in the plasma supernatant and existed in several different types and sizes as identified by Trypan blue staining, cell surface markers and flow cytometry. Through these methods, it was determined that the isolated Nuc-P2s with a size of 0.1 to 2.0 microns having cell surface markers CD66e, Carcinoembryonic Antigen (CEA) and Carcinoembryonic Antigen Cell Adhesion Molecule-1 (CEA-CAM-1) exhibited the characteristics of totipotent stem cells (Nuc-P2s$_{0.1-2.0}$). It was further determined that the Nuc-P2s with a size of >2.0 to <4.0 microns and >4.0 to <6.0 microns and having surface markers CD66e, CEA, CEA-CAM-1, CD10, and Stage Specific Embryonic Antigen (SSEA) exhibited characteristics of transitional-totipotent stem cells to pluripotent stem cells, (Nuc-P2s>2-<4, Nuc-P2s>4-<6). It was further determined that the nucleated plasma particles having surface markers CD10 and SSEA with a size of 6.0 to 8.0 microns exhibited the characteristics of pluripotent stem cells (Nuc-P2s$_{6-8}$). It was further determined that the Nuc-P2s having surface markers CD10, SSEA, CD90 and Thy-1 with a size of >8.0 to <10.0 microns exhibited the characteristics of transitional-pluripotent stem cell/germ layer lineage stem cells (Nuc-P2s$_{>8-<10}$), which is a transitional population between pluripotent Nuc-P2s$_{6-8}$ and lineage-specific ectodermal stem cells (EctoSCs), mesodermal (mesenchymal) stem cells (MesoSCs$_{10-12}$), and endodermal stem cells (EndoSCs).

Utilizing this information, the subject invention details a method and system for optimizing the isolation and delivery of adult blood-derived MesoSCs and Nuc-P2s of animal origin (human, non-human mammal, non-mammalian animal) for treatment of damaged tissue.

The present method entails the administration of one or more stimulators to a blood source (for example, a human or nonhuman mammal or non-mammalian animal) to prompt Nuc-P2s located in connective tissue to proliferate. Such stimulators include, but not be limited to antioxidants and flavonoids. The antioxidant and flavonoid stimulators include, but are not limited to fresh, frozen, and powdered blueberries, raspberries, blackberries, and concord grapes. The dosage range is based upon the weight of the recipient; by way of a non-limiting example, 1 teaspoon to 10 cups of blueberries or powdered equivalent per day for a minimum of 30 days with a preferred dose of ½ to 1 cup of blueberries, frozen/thawed blueberries or powdered equivalent per day per one hundred to two hundred pound subject.

The present method also entails the administration of one or more mobilizers to a blood source to cause MesoSCs and Nuc-P2s located in the connective tissue to migrate into the peripheral vasculature of the blood source. Such mobilizers include the Cyanobacter Aphanizomenon tios-aquae, exercise and physical trauma. The dosage for Cyanobacter Aphanizomenon flos-aquae is based upon the weight of the blood source; by way of a non-limiting example, the dosage is about 1 to about 10 capsules (one capsule containing 500 milligrams), with a preferred dose of 2 capsules per one hundred to two hundred pound subject, taken within a range of about 1 to about 24 hours before nucleated plasma particle harvest, with a preferred time of 18 hours before harvest. The exercise dosage is about 1 minute to about 5 hours of light (aerobic—walking, swimming) to heavy (weight lifting) exercise, with a minimum of 10 minutes of light exercise). The amount of physical trauma is sufficient where the basement membrane between tissue layers is compromised. This occurs when there is bleeding into tissues outside the vasculature, such as wounds through the skin; tears in muscle, tendons, ligaments, and organs; fractures in bone; second and third degree burns; myocardial infarction; ulcers; and the like. Once the MesoSCs and Nuc-P2s have mobilized into the peripheral vasculature of the blood source, a predetermined clinical dose of about 1 to about 100 units sodium heparin per kilogram bodyweight, preferably an intravenous bolus of 40 units of heparin per Kg individual or a maximum dosage of 4000 units is administered to the blood source to prevent clotting from interfering with collection of the MesoSCs and Nuc-P2s in the blood source. This heparin dose is generally dispensed in 100 units/cc (1 cc is equivalent to 1 ml) such that the bolus in the case of 4000 units is 40 cc given IV push over about 5 minutes to about 15 minutes, with a preferred time of 10 minutes. If it is determined the patient is in need of hydration this dose may be mixed with about 250 cc to about 500 cc of normal saline, with a preferred volume of 350 cc and given over about 15 minutes to about 60 minutes, with preferred time of 30 minutes prior to harvest as a short drip. It may be necessary to modify total volume and preferred time of infusion in patients with cardiovascular or renal conditions. Heparin doses should be used with caution or avoided in recipients with stroke; active bleeding, or recipients who are determined to be of high bleeding risk or, in the case of juvenile or premature neonatal recipients.

The administration of sodium heparin operates such that when a platelet encounters a break in the endothelium, as would be created with the insertion of a needle, Tissue Factor activates the coagulation pathway leading to the production of thrombin; and the subsequent conversion of fibrinogen to fibrin. Fibrin and collagen are then exposed to blood proteins and platelets triggering their activation and clotting activity. The Heparin further operates to bind to anti-thrombin (also known as AT-III), to drastically accelerate the ability of anti-thrombin to bind Factor Xa, thus neutralizing Factor Xa's effect on the coagulation cascade. The heparin preparation being administered to the recipient is able to neutralize both Factor Xa and Thrombin; shutting down thrombin's ability to convert fibrinogen to fibrin and lessening the propagation of platelet and coagulation activation associated with trauma. By way of a non-limiting example, such a trauma might be the insertion of a needle into a blood vessel. Further, at a bolus heparin dosage of 75 units/kg, the majority of recipients should be completely anticoagulated. Preferably, an anticoagulation monitoring of recipients is performed following standard protocols as known to those skilled in the art.

The method of the present invention utilizes a clinically determined amount of sodium heparin of about 1 unit to about 100 units per Kg bodyweight per recipient, (maximum total bolus dose of 15,000 units), preferably 10 units sodium heparin per Kg bodyweight per recipient up to a preferred maximum of 4,000 units administered intravenously to the blood source, to prevent coagulation impeding circulation of nucleated plasma particles in the blood source.

A blood sample is removed from the blood source by sterile venipuncture. In a non-limiting example, the volume of such a blood sample is between about 1 ml and 500 ml for a human, or about 3000 ml for a large mammal such as an equine, In another non-limiting example, when the damaged tissue to be treated is nerve tissue, brain tissue, respiratory, cardiovascular, gastrointestinal, genitourinary, or endocrine organ, the preferred blood sample volume is 200 ml/month per blood draw over 2 months for a human or 1500 ml/month per blood draw over two months for a large non-human mammal. In another non-limiting example, when the damaged tissue to be treated is muscle, intervertebral discs, tendons, ligaments or joints, the preferred blood sample volume is 100 ml for a human or 1000 ml for a large non-human mammal. The blood sample is placed into one or more containers containing a divalent cation chelating agent, such as Ethylenediaminetetraacetic acid ("EDTA") or Ethyleneglycol bis (2-Aminoethyl ether)-N,N,N',N' tetraacetic acid ("EGTA") or equivalent calcium chelating agent. Treating the blood sample with EDTA (or EGTA or equivalent calcium chelating agent) removes divalent calcium cations from the surface of the nucleated plasma particles by chelation, restoring the zeta potential of the MesoSCs and Nuc-P2s, thereby opening up binding sites for inductive factors, proliferation agents, collagens, and other extracellular matrix materials. Restoration of the zeta potential also allows for future attachment to damaged tissue, and cellular proliferation and differentiation into selected cell types within the damaged tissues.

Restoration of the MesoSCs' and Nuc-P2s' zeta potential, also allows the separation of the MesoSCs and Nuc-P2s from the remaining blood components (red blood cells, white blood cells, platelets) by their charge differential and inherent densities.

It was unexpectedly discovered that restoration of MesoSCs' and Nuc-P2s' zeta potential by chelation and resetting of MesoSCs' and Nuc-P2s' proliferation rate by refrigeration, when coupled with differential centrifugation, proves superior to previous isolation methods using enzymes, because MesoSCs and all sub-types of Nuc-P2s present in the blood sample, such as, $Nuc\text{-}P2_{0.1\text{-}2.0}$, $Nuc\text{-}P2_{>2\text{-}<4}$, $Nuc\text{-}P2_{>4\text{-}<6}$, $Nuc\text{-}P2_{6\text{-}8}$, and $Nuc\text{-}P2_{>8\text{-}<10}$, were intact and can be used either singly or in combination for treatment of damaged tissues. This is accomplished by storing the containers containing the blood-EDTA (or blood-EGTA or blood-chelator equivalent) mixture for about 1 minute to about 72 hours or longer at a temperature about 2 to about 8 degrees Centigrade to allow gravity sedimentation to take place. The preferred times are 6 hours, 12 hours, 36 hours and 72 hours (dependent on species) at a preferred temperature of 4 degrees Centigrade if no centrifugation is used. If centrifugation is used, the containers holding the blood-EDTA (or blood-EGTA or blood-calcium-chelator equivalent) mixtures are mixed and the containers are stored for a minimum of about 1 minute to about 24 hours, with a preferred time of 2 hours total cumulative time at a temperature about 2 to about 8 degrees Centigrade, at a preferred temperature of 4 degrees Centigrade. Centrifugation occurs at about 200 to about 20,000 times gravity (xg) or relative centrifugation force (RCF) with preferred centrifugation speeds of 3500xg or 3500 RCF (see Table 1, CF1), 500xg or 500 RCF (see Table 1, CF2B), 4500xg or 4500 RCF (see Table 1, CF2A), 6000xg or 6000 RCF (see Table 1, CF3A), 7000xg or 7000 RCF (see Table 1, CF4A), 8000xg or 8000 RCF (see Table 1, CF5A), and/or 13,000xg or 13,000 RCF (see Table 1, CF6A). The reduction in temperature resets the MesoSCs' and Nuc-P2s' proliferation rate, ensuring the MesoSCs and Nuc-P2s will obtain optimum proliferation rates of 18-24 hours for MesoSCs and 12 to 16 hours for Nuc-P2s per cell doubling when they are reintroduced into an environment at normal recipient body temperature.

TABLE 1

Centrifugation Speeds to Derive Nuc-P2s and MesoSCs for Treatment Protocols

| CF# | First Spin (CF) xg/RCF | First Spin Pellet | First Spin Supernatant | Second Spin xg/RCF | Second Spin Pellet | Second Spin Supernatant |
|---|---|---|---|---|---|---|
| CF1, PG | 3,500 or gravity sedimentation | RBCs, WBCs, Platelets, MesoSCs 10-12 microns (CF1B) | Nuc-P2s 0.1-<10 microns (CF1A) | Variable | Populations of Nuc-P2s 0.1-<10 microns | — |
| CF2A, PG | ~4,500 | Nuc-P2s 8-<10 microns | Nuc-P2s 0.1-<8, microns | 13,000 | Nuc-P2s 0.1-<8 microns | — |
| CF2B, SG | ~300 | RBCs, WBCs, Platelets | MesoSCs 10-12 microns | ~1,000 | MesoSCs 10-12 microns | — |
| CF3B, SG | ~1,000 | MesoScs 10-12 microns | — | — | — | — |
| CF3A, PG | ~6,000 | Nuc-P2s 6-<10 microns | Nuc-P2s 0.1-<6 microns | 13,000 | Nuc-P2s 0.1-<6 microns | — |
| CF4A, PG | ~7,000 | Nuc-P2s >4-<10 microns | Nuc-P2s 0.1-<4 microns | 13,000 | Nuc-P2s 0.1-<4 microns | — |

TABLE 1-continued

Centrifugation Speeds to Derive Nuc-P2s and MesoSCs for Treatment Protocols

| CF# | First Spin (CF) xg/RCF | First Spin Pellet | First Spin Supernatant | Second Spin xg/RCF | Second Spin Pellet | Second Spin Supernatant |
|---|---|---|---|---|---|---|
| CF5A, PG | ~8,000 | Nuc-P2s >2-<10 microns | Nuc-P2s 0.1-2.0 microns | 13,000 | Nuc-P2s 0.1-2.0 microns | — |
| CF6A, PG | ~13,000 | Nuc-P2s 0.1-<10 microns | — | — | — | — |

CF#, Flow chart steps to derive MesoSCs and/or Nuc-2P2s from whole blood; CF, Centrifugation Force; xg, times gravity; RCF, Relative Centrifugal Force; PG, Plasma Gradient; SG, Saline Gradient The present invention also encompasses several embodiments optimizing effective reintroduction of MesoSCs and Nuc-P2s to damaged tissue. The initial step is clinical screening to exclude recipients with a history of active neoplasms and examination of the patient to determine the damaged tissue to be treated.

Individual populations of MesoSCs and Nuc-P2s can be derived by sequential centrifugation steps. This is accomplished by centrifuging the blood-EDTA (or blood-EGTA or blood-calcium chelator equivalent) mixture for about 1 minute to about 10 minutes, preferably 8 minutes, at a speed of about 200 to 20,000 RCF, preferably 3,500 RCF (see Table 1, CF1). This centrifugation creates pellet CF1B which contains RBCs, WBCs, Platelets, and $MesoSCs_{10-12}$ (see Table 1, CF1B) and supernatant CF1A containing $Nuc-P2s_{0.1-<10}$ (see Table 1, CF1A). Individual and separate populations of Nuc-P2s, $Nuc-P2s_{>8-<10}$, $Nuc-P2s_{6-8}$, $Nuc-P2s_{>4-<6}$, $Nuc-P2s_{>2-<4}$, and $Nuc-P2s_{0.1-2.0}$, can be obtained by sequential centrifugation steps (see Table 1, CF2, CF3, CF4, CF5 and CF6). The $Nuc-P2s_{>8-<10}$ can be further separated from the remaining Nuc-P2s ($Nuc-P2s_{0.1-<8}$) by centrifuging supernatant CF1A for 1 to 10 minutes, preferably 5 minutes, at a speed of about 200 RCF to about 20,000 RCF, preferably 4,500 RCF creating pellet CF2A, which contains $Nuc-P2s_{>8-<10}$ and supernatant CF2A which contains $Nuc-P2s_{0.1-<8}$ (see Table 1, CF2A). The $Nuc-P2s_{6-8}$ can be further separated from the remaining Nuc-P2s ($Nuc-P2s_{0.1-<6}$) by centrifuging supernatant CF2A for 1 to 10 minutes, preferably 5 minutes, at a speed of about 200 RCF to about 20,000 RCF, preferably 6,000 RCF creating pellet CF3A, which contains $Nuc-P2s_{6-8}$ and supernatant CF3A which contains $Nuc-P2s_{0.1-<6}$ (see Table 1, CF3A). The $Nuc-P2s_{>4-<6}$ can be further separated from the remaining Nuc-P2s ($Nuc-P2s_{0.1-<4}$) by centrifuging supernatant CF3A for 1 to 10 minutes, preferably 5 minutes, at a speed of about 200 RCF to about 20,000 RCF, preferably 7,000 RCF creating pellet CF4A, which contains $Nuc-P2s_{>4-<6}$ and supernatant CF4A which contains $Nuc-P2s_{0.1-<4}$ (see Table 1, CF4A). The Nuc-P2s>2-<4 can be further separated from the remaining Nuc-P2s ($Nuc-P2s_{0.1-2.0}$) by centrifuging supernatant CF4A for 1 to 10 minutes, preferably 5 minutes, at a speed of about 200 RCF to about 20,000 RCF, preferably 8,000 RCF creating pellet CF5A, which contains $Nuc-P2s_{>2-<4}$ and supernatant CF5A which contains $Nuc-P2s_{0.1-2.0}$ (see Table 1, CF5A). The $Nuc-P2s_{0.1-2.0}$ can be isolated by centrifuging supernatant CF5A for 1 to 10 minutes, preferably 5 minutes, at a speed of about 200 RCF to about 20,000 RCF, preferably 13,000 RCF creating pellet CF6A, which contains $Nuc-P2s_{0.1-2.0}$ and supernatant CF6A which is void of Nuc-P2s (see Table 1, CF6A). $MesoSCs_{10-12}$ can be separated from RBCs, WBCs, and Platelets by eliminating the plasma gradient and substituting a saline gradient prior to centrifugation. This is performed by re-suspending the CF1B pellet in a minimal ratio of 1 pellet volume cells to 5 pellet volumes of sterile saline. The re-suspended mixture is centrifuged for 1 to 10 minutes, preferably 5 minutes, at a speed of about 200 RCF to about a speed of 20,000 RCF, preferably 300 RCF creating pellet CF2B (see Table 1, CF2B). The $MesoSCs_{10-12}$ can be isolated by centrifuging supernatant CF2B for 1 to 10 minutes, preferably 5 minutes, at a speed of about 200 RCF to about a speed of 20,000 RCF, preferably 1,000 RCF creating pellet CF3B (see Table 1, CF3B). Alternatively, if batch processing of $MesoSCs_{10-12}$ and Nuc-P2s is desired to pool designated populations, sequential centrifugation steps are not necessary. Rather, the isolated stem cells can be processed as discussed in the following embodiments of the invention.

As illustrated in FIG. 1, in a preferred embodiment of the invention wherein the damaged tissue to be treated is central nervous system tissue, and the cells administered are autologous. A blood sample is removed from a blood source step 302. The blood sample is then mixed with EDTA (or EGTA or equivalent calcium chelating agent) step 304. The $MesoSCs_{10-12}$ and $Nuc-P2s_{0.1-<10}$ in the blood-EDTA (or blood-EGTA or blood-equivalent) mixture are isolated by differential centrifugation. This is accomplished by centrifuging the blood-EDTA (or blood-EGTA or blood-equivalent) mixture for about 1 minute to about 10 minutes, preferably 8 minutes, at a speed from about 200 RCF to about 20,000 RCF, preferably 3,500 RCF (see Table 1, CF1) step 306. This centrifugation creates a pellet, pellet CF1B, which contains (RBCs, WBCs, Platelets, and $MesoSCs_{10-12}$), (see Table 1, CF1B) and a supernatant, supernatant CF1A, containing $Nuc-P2s_{0.1-<10}$ (see Table 1, CF1) step 306. The $Nuc-P2s_{0.1-2.0}$ are further separated from the remaining Nuc-P2s ($Nuc-P2_{>2-<10}$) by centrifuging supernatant CF1A for 1 minute to 10 minutes, preferably 5 minutes, at a speed of about 200 RCF to about 20,000 RCF, preferably 8,000 RCF, creating first spin pellet CF5, which includes $Nuc-P2s_{>2-<10}$ and supernatant CF5A, step 308. Supernatant CF2A is centrifuged for about 1 minute to about 10 minutes, preferably 5 minutes, at a speed of about 200 RCF to 20,000 RCF, preferably 4,500 RCF, creating pellet CF3A and supernatant CF3A, step 310. Supernatant CF3A is centrifuged for about 1 minute to about 10 minutes, preferably 5 minutes, at a speed of about 200 RCF to 20,000 RCF, preferably 6,000 RCF, creating pellet CF4A and supernatant CF4A, step 312. Supernatant CF4A is centrifuged for about 1 minute to about 10 minutes, preferably 5 minutes, at a speed of about 200 RCF to 20,000 RCF, preferably 7,000 RCF, creating a second spin pellet CF5A, which includes Nuc-P2s$_{>8-<10}$, Nuc-P2s$_{6-8}$, Nuc-P2s$_{>4-<6}$, and Nuc-P2s$_{>2-<4}$, and a second spin supernatant CF5A which includes Nuc-P2s$_{0.1-2.0}$, (see Table 1, CF5A), step 314. Supernatant CF5A consists essentially of Nuc-P2s with a size between 0.1 microns to 2.0 microns and exhibiting the characteristics of totipotent Nuc-P2s$_{0.1-2.0}$. Supernatant CF5A is centrifuged for about 1 minute to about 10 minutes, preferably 5 minutes, at a speed of about 200 RCF to about. 20,000 RCF, preferably 13,000 RCF, creating pellet CF6A and supernatant CF6A step 316 (see Table 1, CF6A). Pellet CF6A, which includes Nuc-P2s$_{0.1-2}$, is re-suspended in a clinically determined volume of volume of about 0.01% to about 2% sterile saline with a preferred concentration of 0.9% sterile saline, step 318. The re-suspended pellet CF6A-saline composition is administered to the recipient by intra-nasal topical application step 320.

Prior to administration of the re-suspended pellet CF6A-saline composition (containing Nuc-P2s$_{0.1-2}$) to the recipient, a nasal wash of 0.01% to 2% sterile aqueous sodium chloride with a preferred concentration of 0.65% sodium chloride with sodium phosphate, sodium hydroxide, phenylcarbinol, and benzalkonium chloride is administered to the recipient to remove the mucous layer. The recipient is placed in the reverse Trendelenburg position, and the 0.9% saline re-suspended pellet CF6A (Nuc-P2s$_{0.1-2}$) composition is administered by topical application onto the olfactory mucosa. Without the impedance of the mucous layer, the Nuc-P2s$_{0.1-2}$ migrate between the olfactory mucosa cells, along the olfactory nerve rootlets, through the cribriform plate, along the olfactory nerves, and into the cisterns surrounding the central nervous system, thus by-passing the blood-brain barrier, and subsequently migrate to the site of damaged brain tissue and/or spinal cord tissue.

The cell pellet CF1B from FIG. 1 step 306, consists essentially of MesoSCs$_{10-12}$, RBCs, WBCs, and platelets. As illustrated in FIG. 1*a*, the MesoSCs$_{10-12}$ are separated from the RBCs, WBCs, and platelets by re-suspending the cell pellet, CF1B from FIG. 1 step 306 in a 5 times pellet volume of about 0.1% to 2% sterile saline, preferably 0.9% sterile saline and is pulse vortexed (at a setting between about 1 to about 10 with a preferred setting of 6-8) three times to create a first composition FIG. 1*a*, step 402. The first composition is centrifuged for about 1 minute to 60 minutes, preferably 5 minutes at about 200 RCF to 20,000 RCF, preferably 300 RCF, creating pellet CF2B (RBCs, WBCs, platelets) and supernatant CF2B (MesoSCs$_{10-12}$) (see Table 1, CF2B) step 404. Supernatant CF2B (containing MesoSCs$_{10-12}$) is centrifuged for about 1 minute to about 10 minutes, preferably 5 minutes, at a speed of about 200 RCF to about 20,000 RCF, preferably 1,000 RCF, creating pellet CF3B and supernatant CF3B (see Table 1, CF3B) step 406.

Sodium heparin is added to a clinically predetermined volume of sterile saline to create a mixture; with the sterile saline having a concentration of about 0.01% to about 2% sterile saline, with a preferred concentration of 0.9% sterile saline and the sodium heparin dosage being about 1,000 units of heparin regardless of the volume of sterile saline, with a preferred volume of about 500 ml step 408. The pellets CF3B, which includes MesoSCs$_{10-12}$ and CF5A (see Table 1, CF3B-first spin pellet) are re-suspended in a clinically determined volume of about 0.01% to 2% sterile saline with a preferred concentration of about 0.9% sterile saline, and pooled step 410. The re-suspended pellets are added to the sodium heparin-saline mixture to create a second composition step 412.

The second composition containing reconstituted MesoSCs$_{10-12}$, Nuc-P2s$_{>2-<10}$, 0.9% sterile saline and sodium heparin having a preferred concentration of about 1,000 units heparin per 500-ml of 0.9% sterile saline is administered to the recipient intravenously at a slow drip rate step 414. The amount of heparin added; however, is not necessarily dependent on intravenous bag and stem cell volume, but rather on the weight of the patient. The drip rate being about 100-ml to about 1000-ml per hour and at a preferred drip rate of 500-ml per hour. The sodium heparin prevents clot formation during administration of the composition. The tissues outside the vasculature contain collagens and extracellular matrix macromolecules that function to aid in the attachment of the MesoSCs$_{10-12}$ and Nuc-P2s$_{>2-<10}$ to the damaged tissues. This separate administration of the larger MesoSCs$_{10-12}$ and Nuc-P2s$_{>2-<10}$ to the recipient intravenously reduces the likelihood of the recipient's body diverting the smaller site-directed Nuc-P2s$_{0.1-2}$ for use in other parts of the body by making the MesoSCs$_{10-12}$ and larger Nuc-P2s$_{>2-<10}$ available for that purpose. As a benefit of this method, the maximum number of site-directed Nuc-P2s are available for tissue repair at the specific directed site.

MesoSCs exhibit cell surface MHC-I and HLA-DR-II antigens whereby a competent immune system can recognize self (recipient) versus non-self (blood source), and elicit an immune response if the cells are recognized as non-self. Therefore, if allogeneic MesoSCs are to be considered for transplant, both the blood source and the recipient need to be haplotyped to ascertain the compatibility of the allogeneic MesoSCs for transplant. If the haplotypes are either unknown or do not match, then the allogeneic blood source MesoSCs are not utilized. In contrast, Nuc-P2s do not display either MHC-I and/or HLA-DR-II cell surface antigens. Therefore, allogeneic Nuc-P2s can be utilized for allogeneic donation. However, allogeneic plasma contains proteins, such as immunoglobulins, that can recognize self (blood source) from non-self (recipient) and must be removed prior to transplant to prevent an immune reaction culminating in a graft versus host disease. Therefore, whenever allogeneic haplotyped-matched MesoSCs and/or Nuc-P2s are utilized the donor allogeneic cells are washed extensively to remove plasma proteins that may adhere to the cells and potentially cause a graft versus host response.

In another preferred embodiment, where the tissue to be repaired is damaged central nervous system tissue (brain and/or spinal chord), and the optimally isolated MesoSCs and/or Nuc-P2s are allogeneic, the blood-chelating agent mixture is centrifuged for about 1 minute to about 10 minutes, preferably 8 minutes, at about 200 RCF to about 20,000 RCF, preferably 3,500 RCF to create a cell pellet (cell pellet CF1B), containing RBCs, WBCs, Platelets and, optionally haplotyped-matched MesoSCs$_{10-12}$ and a supernatant (supernatant CF1A), which contains Nuc-P2s$_{0.1-<10}$ (see Table 1, CF1). Supernatant CF1A is centrifuged again at about 200 RCF to about 20,000 RCF, preferably 8,000 RCF, creating a pellet (CF5A), containing Nuc-P2s$_{>2.0-<10}$ and a supernatant (CF5A), containing Nuc-P2s$_{0.1-2.0}$ (see Table 1, CF5A first and second spin pellets). Supernatant CF5A is centrifuged again at about 200 RCF, to about 20,000 RCF, preferably 13,000 RCF to create a pellet (CF6A), containing Nuc-P2s$_{0.1-2.0}$. Pellet CF6A is re-suspended in a minimum of 1:5 ratio of a clinically determined volume of about 0.01% to 2% sterile saline with a preferred concentration of about 0.9% sterile saline. (If there are multiples of pellet CF6, the re-suspended pellets are pooled.) The re-suspended pellet(s) is centrifuged at about 200 RCF to about 20,000 RCF, preferably 13,000 RCF to create another pellet and supernatant (see Table 1, CF5A). This process of re-suspending the pellet in a minimum 1:5 ratio (1 volume pellet to 5 volumes saline) of 0.9% sterile saline is repeated a second time to insure that the allogeneic plasma proteins are removed from the cells. The supernatant is decanted and the pellet is re-suspended to a final volume of about 0.4 ml in about 0.9% sterile saline. The Nuc-$P2s_{0.1-2.0}$-saline composition is administered to the recipient by intra-nasal topical application with about 0.2 ml applied to each nostril.

The first spin pellet(s) CF5A, containing allogeneic Nuc-$P2s_{>2.0-<10}$ (see Table 1, CF5A) and, optionally, haplotyped-matched allogeneic $MesoSCs_{10-12}$ (see Table 1, CF3B) are re-suspended in about 0.9% sterile saline with a 1:5 pellet to saline ratio. If there are multiple CF5A pellets, each of the re-suspended CF5A and CF3B pellets are pooled together. The re-suspended pellets(s) are pooled and centrifuged at about 200 RCF to about 20,000 RCF, preferably 13,000 RCF to create a pellet and supernatant. The supernatant is discarded and the pellet is re-suspended in about 0.9% sterile saline in a 1:5 pellet to saline ratio. The re-suspended pellet is centrifuged again at about 200 RCF to about 20,000 RCF, preferably 13,000 RCF, creating a final pellet and supernatant. The supernatant is discarded and the final pellet is re-suspended in about 0.9% sterile saline for a final volume of about 25 ml; and is added to a clinically predetermined volume of about 0.9% saline and sodium heparin and having a final concentration range of about 1 unit to about 100 units of heparin with a preferred concentration of about 12 units per Kg bodyweight up to a maximum of about 1,000 units of heparin regardless of volume sterile saline with a preferred volume of about 500-ml to create a composition which is administered to the recipient intravenously in the manner of above. The additional wash of the allogeneic Nuc-$P2s_{0.1-2.0}$ and Nuc-$P2s_{>2-<10}$ (and optionally haplotyped-matched $MesoSCs_{10-12}$) with 0.9% sterile saline removes allogeneic plasma (serum) proteins such as immunoglobulins, thereby reducing the likelihood of rejection of the $MesoSCs_{10-12}$ and Nuc-$P2s_{>2-<10}$ by the recipient's immune system.

FIG. 2 illustrates a preferred embodiment of the invention wherein the damaged tissue to be treated is respiratory system tissue and the MesoSCs and Nuc-P2s to be administered are autologous. A blood sample is removed from a blood source in the manner described in above step 502. The blood sample is then mixed with a chelating agent such as EDTA (or EGTA or equivalent calcium chelating agent) as also described in above step 504. The $MesoSCs_{10-12}$ and Nuc-P2s in the blood-EDTA (or EGTA or blood-calcium chelator equivalent) mixture are isolated by differential centrifugation to create pellet CF1B (RBCs, WBCs, Platelets, and $MesoSCs_{10-12}$) and supernatant CF1A (Nuc-$P2s_{0.1-<10}$), (see Table 1, CF1A, CF1B) step 506. This is accomplished by centrifuging the blood-EDTA (or blood-EGTA or blood-calcium chelator equivalent) mixture for about 1 minute to about 10 minutes, preferably 8 minutes, at a speed from about 200 RCF to about 20,000 RCF, preferably 3,500 RCF (see Table 1, CF1). The pellet CF1B contains the $MesoSCs_{10-12}$, as well as RBCs, WBCs, and platelets, whereas supernatant CF1A contains the Nuc-$P2s_{0.1-<10}$.

Supernatant CF1A is further subdivided by differential centrifugation into Nuc-$P2s_{0.1-8}$ creating pellet CF2A containing Nuc-$P2s_{>8-<10}$ and Nuc-$P2s_{0.1-8}$ (see Table 1, CF2A) step 508. This step, 508, is accomplished by centrifuging supernatant CF1A for about 1 minute to about 10 minutes, preferably 5 minutes, at a speed of about 200 RCF to about 20,000 RCF, preferably 4,500 RCF (see Table 1, CF2A). Supernatant CF2A contains Nuc-$P2s_{0.1-<8}$ exhibiting the characteristics of totipotent Nuc-$P2s_{0.1-2}$ and pluripotent Nuc-$P2_{>2-<4}$, Nuc-$P2_{>4-<6}$ and Nuc-$P2s_{-6-8}$ which are further isolated by differential centrifugation step 510. This step, 510, is accomplished by centrifuging the supernatant CF2A (Nuc-$P2s_{0.1-8}$) for about 1 minute to about 10 minutes, preferably 5 minutes, at a speed of about 200 RCF to about 20,000 RCF, preferably 13,000 RCF (see Table 1, CF2A—2nd spin pellet), to create second spin pellet CF2A containing Nuc-$P2s_{0.1-8}$ and 2nd spin supernatant CF2A. Second (2nd) spin pellet CF2A is re-suspended in a clinically determined amount of about 0.01% to about 2% sterile saline with a preferred concentration of 0.9% sterile saline to create a composition step 512. The Nuc-$P2s_{0.1-8}$/0.9% saline composition is administered to the recipient by nebulization step 514.

Figure 2A:
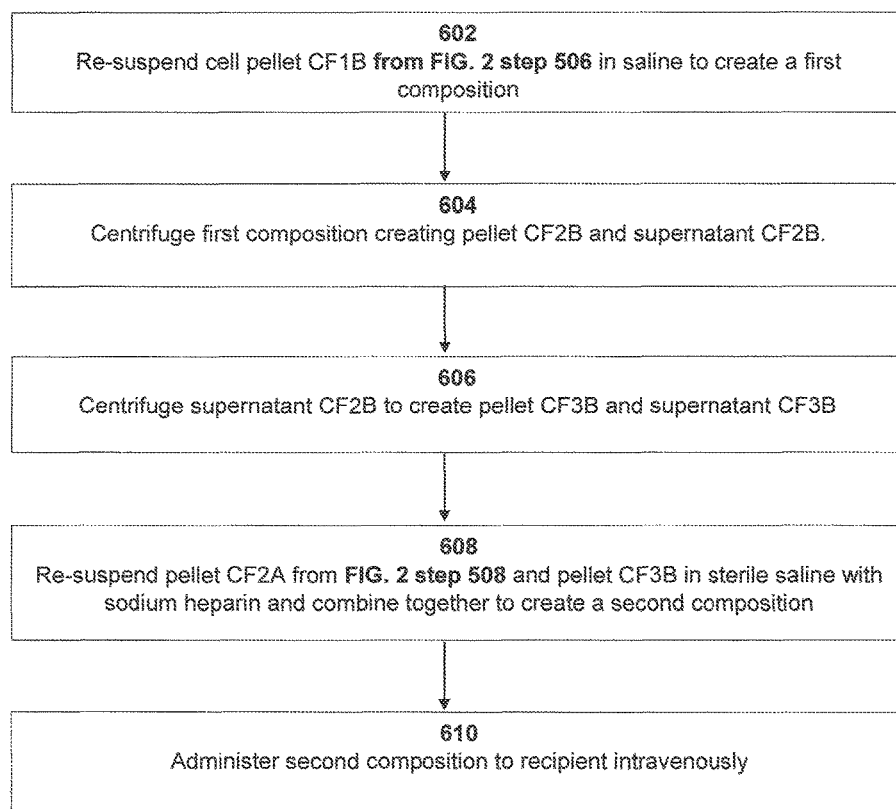
FIG. 2a is a continuation from FIG. 2 of the optimal isolation of MesoSCs and Nuc-P2s from whole blood where the damaged tissue to be treated is respiratory tissue, beginning with cell pellet CF1B through administering a composition to the recipient intravenously.

As illustrated in FIG. 2a, the larger stem cells, such as $MesoSCs_{10-12}$ and Nuc-$P2s_{>8-<10}$ are isolated and administered to the recipient intravenously. The $MesoSCs_{10-12}$ are separated from the RBCs, WBCs, and platelets by re-suspending the cell pellet CF1B from FIG. 2 step 506 in sterile saline to create a first composition FIG. 2a, 602. The first composition in step 602 is created by adding 5 times pellet volume of about 0.1% to about 2% sterile saline, preferably 0.9% sterile saline and pulse vortexing (at a setting between about 1 to about 10 with a preferred setting of 6-8) three times. The first composition (CF1B-saline) is centrifuged for about 1 minute to about 10 minutes, preferably 5 minutes at about 200 RCF to about 20,000 RCF, preferably 300 RCF (see Table 1, CF2B), creating pellet CF2B (containing RBCs, WBCs, platelets) and supernatant CF2B (containing $MesoSCs_{10-12}$) step 604. Supernatant CF2B, containing the $MesoSCs_{10-12}$ is centrifuged CF2B for about minute to about 10 minutes, preferably 5 minutes, at a speed of about 200 RCF to about 20,000 RCF, preferably 1,000 RCF (see Table 1, CF3B) to create pellet CF3B and supernatant CF3B step 606. Pellet CF3B containing MesoSCs and pellet CF2A from FIG. 2 step 508 containing Nuc-P2s>8-<10 are re-suspended in a clinically determined volume of sterile saline and pooled together creating a second composition FIG. 2a step 608. The second composition has a concentration of about 0.1% to about 2% sterile saline with a preferred concentration of 0.9% sterile saline. Sodium heparin is added to a volume of sterile saline having a dose range of heparin of about 1 unit to about 200 units/kg of recipient bodyweight with a preferred dosage of 12 units/kg bodyweight up to a maximum of 1,000 units heparin per about 1 ml to about 2,000 ml of sterile saline with a preferred volume of 500 ml of sterile saline. Thus, in most cases the preferred mixture is 1000 units of heparin in 500 cc of sterile normal saline to which the second composition is added.

The second composition containing the $MesoSCs_{10-12}$, and Nuc-$P2s_{>8-<10}$ re-suspended in 0.9% sterile saline and sodium heparin having a preferred concentration of about 1,000 units heparin per about 2,000-ml of sterile saline with a preferred volume of 500-ml is administered to the recipient intravenously at a moderate drip rate step 610. The intravenous drip rate being about 100-ml to about 1000-ml per hour and at a preferred drip rate of 500-ml per hour. It may be necessary to modify total volume and preferred time of infusion in patients with cardiovascular or renal conditions. The sodium heparin prevents clot formation during administration of the composition. The tissues outside the vasculature contain collagens and extracellular matrix macromolecules that function to aid in the attachment of the $MesoSCs_{10-12}$ and Nuc-$P2s_{>8-<10}$ to the damaged tissues.

MesoSCs exhibit cell surface MHC-I and HLA-DR-II antigens whereby a competent immune system can recognize self (recipient) versus non-self (blood source) and elicit an immune response, if the cells are recognized as non-self. Therefore, if allogeneic MesoSCs are to be considered for transplant both the blood source and the recipient need to be haplotyped to ascertain the compatibility of the allogeneic MesoSCs for transplant. If the haplotypes are either unknown or do not match, then the allogeneic blood source MesoSCs are not utilized. In contrast, Nuc-P2s do not display either MHC-I and/or HLA-DR-II cell surface antigens. Therefore, allogeneic Nuc-P2s can be utilized for allogeneic donation. However, allogeneic plasma contains proteins, such as immunoglobulins, that can recognize self (blood source) from non-self (recipient) and must be removed prior to transplant to prevent an immune reaction culminating in a graft versus host disease. Therefore, whenever allogeneic haplotyped-matched MesoSCs and/or Nuc-P2s are utilized the blood source allogeneic cells are washed extensively to remove plasma proteins that may adhere to the cells.

In a preferred embodiment of the invention wherein the damaged tissue to be treated is respiratory system tissue and the optimally isolated Nuc-P2s to be administered to the recipient are allogeneic, the blood-chelating agent mixture is centrifuged for about 1 to 10 minutes, preferably 8 minutes, at about 200 RCF to about 20,000 RCF, preferably 3,500 RCF to create a cell pellet (cell pellet CF1B), containing RBCs, WBCs, Platelets and MesoSCs$_{10-12}$ and a supernatant (supernatant CF1A), which contains Nuc-P2s$_{0.1-<10}$ (see Table 1, CF1 second spin pellet and second spin supernatant). Supernatant CF1A is centrifuged again at about 200 RCF to about 20,000 RCF, preferably 13,000 RCF to create the 2nd spin pellet, containing Nuc-P2s$_{0.1-<10}$, and the 2nd spin supernatant, void of Nuc-P2s (see Table 1, CF1 second spin pellet and second spin supernatant). The second spin pellet CF1 is re-suspended in a minimum of 1:5 ratio of a clinically determined volume of about 0.01% to 2% sterile saline with a preferred concentration of about 0.9% sterile saline (If there are multiples of pellet CF1, the re-suspended pellets are pooled.). The re-suspended second spin pellet(s) CF1 is centrifuged at about 200 RCF to about 20,000 RCF, preferably 13,000 RCF creating another pellet and supernatant. This process of re-suspending the pellet in a minimum 1:5 ratio of 0.9% sterile saline and centrifuging at 13,000 RCF is repeated a second time to insure that the allogeneic plasma proteins are removed from the cells; and, after this second spin, a final supernatant and pellet are created. The final supernatant is discarded and the final pellet is re-suspended in about 5 ml of about 0.9% sterile saline. The re-suspended final pellet-saline composition is divided into a first half of about 2.5 ml and a second half of about 2.5 ml. The first half is administered to the recipient by nebulization.

The second half of the re-suspended final pellet-saline composition (from 2nd spin pellet CF1) containing Nuc-P2s$_{0.1-<10}$ (see Table 1, CF1, 2nd spin pellet), and optionally, haplotype-matched MesoSCs$_{10-12}$ (see Table 1, CF3B) is re-suspended in about 0.9% sterile saline with at 1:5 pellet to saline ratio. (If there are multiple CF1 second spin pellets and/or CF3B pellets, each of the re-suspended CF5A and CF3B pellets are pooled together.) The re-suspended pellet(s) is/are pooled and centrifuged at about 200 RCF to about 20,000 RCF, preferably 13,000 RCF to create a pellet and supernatant. The pellet is added to a clinically predetermined volume of about 0.9% sterile saline and sodium heparin (the sodium heparin being previously added) having a final concentration range of about 1 unit to about 100 units of heparin/kg bodyweight of recipient with a preferred concentration of about 12 units per kilogram bodyweight up to a maximum of about 1,000 units of heparin regardless of volume sterile saline with a preferred volume of about 500 ml to create a final composition, which is administered to the recipient intravenously in the manner of paragraph above. It may be necessary to modify total volume and preferred time of infusion in patients with cardiovascular or renal conditions. The additional wash steps of the allogeneic Nuc-P2s$_{>2-<10}$ (and optionally included haplotype-matched MesoSCs$_{10-12}$) with 0.9% sterile saline removes allogeneic plasma proteins such as immunoglobulins, thereby reducing the likelihood of rejection of the Nuc-P2s$_{>2-<10}$ (and optionally included haplotype-matched MesoSCs$_{10-12}$) by the recipient's immune system.

FIG. 3 illustrates a preferred embodiment of the invention wherein the damaged tissue to be treated is an internal organ or internal organ system such as, by way of a non-limiting example, cardiac, kidney, circulatory system or genitourinary system tissue damage; and the MesoSCs$_{10-12}$ and Nuc-P2s$_{0.1-<10}$ to be administered to the recipient are autologous. A blood sample is removed from a blood source step 702. The blood is mixed with a chelating agent, such as EDTA (or EGTA or calcium chelator equivalent) to create a mixture step 704. The MesoSCs$_{10-12}$ and Nuc-P2s in the blood-EDTA (or blood-EGTA or blood-calcium chelator equivalent) mixture are isolated by differential centrifugation creating pellet CF1B (RBCs, WBCs, Platelets, and MesoSCs$_{10-12}$) and supernatant CF1A (Nuc-P2s$_{-0.1-<10}$) (see Table 1, CF1) step 706. This is accomplished by centrifuging the blood-EDTA (blood-EGTA or blood-calcium chelator equivalent) mixture between about 1 minute to about 10 minutes, preferably 8 minutes at a speed between about 200 to about 20,000, preferably 3,500 RCF. Pellet CF1B contains the MesoSCs$_{10-12}$, as well as RBCs, WBCs, and platelets, whereas supernatant CF1A contains the Nuc-P2s$_{0.1-<10}$ (see Table 1, CF1). The Nuc-P2s$_{0.1-<10}$ are pelleted by centrifuging supernatant CF1A for about 1 minute to about 10 minutes, preferably 5 minutes, at a speed of about 200 RCF to about 20,000 RCF, preferably 13,000 RCF to create 2nd spin pellet CF1A (see Table 1, CF1A) step 708. The MesoSCs$_{10-12}$ are separated from the RBCs, WBCs, and platelets by re-suspending pellet CF1B (from step 706 above) in a 5 times pellet volume of about 0.1% to 2% sterile saline, preferably 0.9% sterile saline to create a first composition step 710. The first composition is centrifuged centrifuging for about 1 minute to about 10 minutes, preferably 5 minutes at about 200 RCF to about 20,000 RCF, preferably 300 RCF (see Table 1, CF2B), creating pellet CF2B (RBCs, WBCs, platelets) and supernatant CF2B (containing MesoSCs$_{10-12}$) (see Table 1, CF2B) step 712. The first composition (supernatant CF2B-saline) is centrifuged for about 1 minute to about 10 minutes, preferably 5 minutes, at a speed of about 200 RCF to about 20,000, preferably 1,000 RCF to create pellet CF3B (see Table 1, CF3B) step 714. The pellet CF3B, which contains MesoSCs$_{10-12}$, and pellet CF6A (from step 708 above) containing Nuc-P2s$_{0.1-<1}$) are each re-suspended and combined in a clinically determined amount of about 0.01% to about 2% sterile saline with a preferred concentration of 0.9% sterile saline to create a second composition step 716. A clinically predetermined amount of sodium heparin is added to 0.1% to 2% sterile saline, preferably 0.9% sterile saline, to which the second composition is added, creating a third composition step 718. The third composition (step 718) is administered intravenously to the recipient step 720. The intravenous drip rate being about 100-ml to about 1000-ml per hour and at a preferred drip rate of 500-ml per hour. The sodium heparin prevents clot formation during administration of the composition. The autologous serum contains fibrinogen that can be converted to fibrin that will physically entrap cells at sites of clot formation. The tissues outside the vasculature contain collagens and extracellular matrix macromolecules that function to aid in the attachment of the MesoSCs$_{10-12}$ and Nuc-P2s$_{0.1-<10}$ to the damaged tissues. The slow intravenous administration allows the MesoSCs$_{10-12}$ and Nuc-P2s$_{0.1-<10}$ maximal time for their exposure to damaged tissue sites. This administration of the MesoSCs$_{10-12}$ and Nuc-P2s$_{0.1-<10}$ to the recipient intravenously allows the recipient's body to use the infused MesoSCs$_{10-12}$ and Nuc-P2s$_{0.1-<10}$ to repair and heal damaged tissues FIG. 3 Also illustrates a preferred embodiment of the invention is where the damaged tissue to be treated is an internal organ or internal organ system such as, by way of a non-limiting example, cardiac, kidney, circulatory system or genitourinary system tissue; and the Nuc-P2s$_{0.1-<10}$ and MesoSCs$_{10-12}$ to be administered to the recipient are allogeneic. MesoSCs$_{10-12}$ exhibit cell surface MHC-I and HLA-DR-II antigens whereby a competent immune system can recognize self (recipient) versus non-self (blood source) and elicit an immune response, if the cells are recognized as non-self. Therefore, if allogeneic MesoSCs$_{10-12}$ are considered for transplant both the blood source and the recipient need to be haplotyped to ascertain the compatibility of the allogeneic MesoSCs$_{10-12}$ for transplant. If the haplotypes are either unknown or do not match, then the allogeneic blood source MesoSCs$_{10-12}$ are not utilized. In contrast, Nuc-P2s do not display either MHC-I and/or HLA-DR-II cell surface antigens. Therefore, allogeneic Nuc-P2s can be utilized for recipient tissue repair. However, allogeneic plasma contains proteins, such as immunoglobulins, that can recognize self (blood source) from non-self (recipient) and must be removed prior to transplant to prevent an immune reaction culminating in a graft versus host disease. Therefore, whenever allogeneic haplotyped-matched MesoSCs$_{10-12}$ and/or Nuc-P2s$_{0.1-<10}$ are utilized the donor allogeneic cells are washed extensively to remove plasma proteins that may adhere to the cells. This preferred embodiment of the invention begins with a blood sample being removed from a blood source step 702. The blood is mixed with a chelating agent, such as EDTA or EGTA (or a calcium chelator equivalent) to create a mixture step 704. The Nuc-P2s$_{0.1-<10}$ (and, optionally, the haplotyped-matched MesoSCs$_{10-12}$) in the blood-EDTA (or blood-EGTA or blood-calcium chelator equivalent) mixture are isolated by differential centrifugation, creating pellet CF1B (RBSs, WBCs, Platelets, and MesoSCs$_{10-12}$) and supernatant CF1A (Nuc-P2s$_{0.1-<10}$) (see Table 1, CF1) step 706. This is accomplished by centrifuging the blood-EDTA (or blood-EGTA or blood-calcium chelator equivalent) mixture between about 1 minute to about 10 minutes, preferably 8 minutes at a speed between about 200 to about 20,000, preferably 3,500 RCF. Pellet CF1B contains the MesoSCs, as well as RBCs, WBCs, and platelets, whereas supernatant CF1A contains the Nuc-P2s$_{0.1-<10}$ (see Table 1, CF1). The Nuc-P2s$_{0.1-<10}$ are pelleted by centrifuging first spin supernatant CF1A for about 1 minute to about 10 minutes, preferably 5 minutes, at a speed of about 200 RCF to about 20,000 RCF, preferably 13,000 RCF to create second spin pellet CF1A (see Table 1, CF1A—second spin pellet) step 708. The (optionally) haplotyped-matched MesoSCs$_{10-12}$ in the blood-EDTA (or blood-EGTA or blood-calcium chelator equivalent) mixture are isolated by differential centrifugation, creating pellet CF1B (RBCs, WBCs, Platelets, and MesoSCs$_{10-12}$) and supernatant CF1A (Nuc-P2s$_{0.1-<10}$) (see Table 1, CF1) in step 706. This is accomplished by centrifuging the blood-EDTA (blood-EGTA or blood-calcium chelator equivalent) mixture between about 1 minute to about 10 minutes, preferably 8 minutes at a speed between about 200 to about 20,000, preferably 3,500 RCF creating a cell pellet (pellet CF1B) and a supernatant (supernatant CF1A). Pellet CF1B contains the MesoSCs$_{10-12}$, as well as RBCs, WBCs, and platelets, whereas supernatant CF1A contains the Nuc-P2s$_{0.1-<10}$ (see Table 1, CF1). The Nuc-P2s$_{0.1-<10}$ are pelleted by centrifuging first spin supernatant CF1A for about 1 minute to about 10 minutes, preferably 5 minutes, at a speed of about 200 RCF to about 20,000 RCF, preferably 13,000 RCF to create second spin pellet CF1A (see Table 1, CF1A second spin pellet) step 708. The (optionally) haplotyped-matched MesoSCs$_{10-12}$ are separated from the RBCs, WBCs, and platelets by re-suspending pellet CF1B (from step 706 above) in a 5 times pellet volume of about 0.1% to 2% sterile saline, preferably 0.9% sterile saline to create a first composition step 710. The first composition is centrifuged for about 1 minute to about 10 minutes, preferably 5 minutes at about 200 RCF to about 20,000 RCF, preferably 300 RCF (see Table 1, CF2B), creating pellet CF2B (RBCs, WBCs, platelets) and supernatant CF2B containing (optionally) haplotyped-matched MesoSCs$_{10-12}$ step 712. The first composition (supernatant CF2B-saline) is centrifuged for about 1 minute to about 10 minutes, preferably 5 minutes, at a speed of about 200 RCF to about 20,000, preferably 1,000 RCF to create pellet CF3B step 714. The pellet CF3B, which contains the (optionally) haplotyped-matched MesoSCs$_{10-12}$, and pellet CF6A (from step 708 above) containing Nuc-P2s$_{0.1-<10}$, are each re-suspended and combined in a clinically determined amount of about 0.01% to about 2% sterile saline with a preferred concentration of 0.9% sterile saline, creating a second composition step 716. The second composition is added to a clinically predetermined amount of sodium heparin enriched sterile normal saline creating a third composition step 718. The third composition having a final concentration range of about 1 unit to about 100 units of heparin/kg bodyweight of recipient with a preferred concentration of about 12 units per kilogram bodyweight up to a maximum of about 1,000 units of heparin regardless of volume sterile saline with a preferred volume of about 500 ml. This third composition is administered intravenously to the recipient at a slow drip rate step 720. The drip rate being about 100-ml to about 1000-ml per hour and at a preferred drip rate of 500-ml per hour. It may be necessary to modify total volume and preferred time of infusion in patients with cardiovascular or renal conditions. The sodium heparin prevents clot formation during administration of the composition. The autologous serum contains fibrinogen that can be converted to fibrin that will physically entrap cells at sites of clot formation. The tissues outside the vasculature contain collagens and extracellular matrix macromolecules that function to aid in the attachment of the allogeneic Nuc-P2s and optionally haplotyped-matched MesoSCs to the damaged tissues. The slow intravenous administration allows the allogeneic Nuc-P2s and potentially haplotyped-matched MesoSCs maximal time for their exposure to damaged tissue sites. The administration of the allogeneic Nuc-P2s and potentially haplotyped-matched MesoSCs to the recipient intravenously allows the recipient's body to use the infused allogeneic Nuc-P2s and optionally haplotyped-matched MesoSCs to repair and heal damaged tissues.

Figure 4:
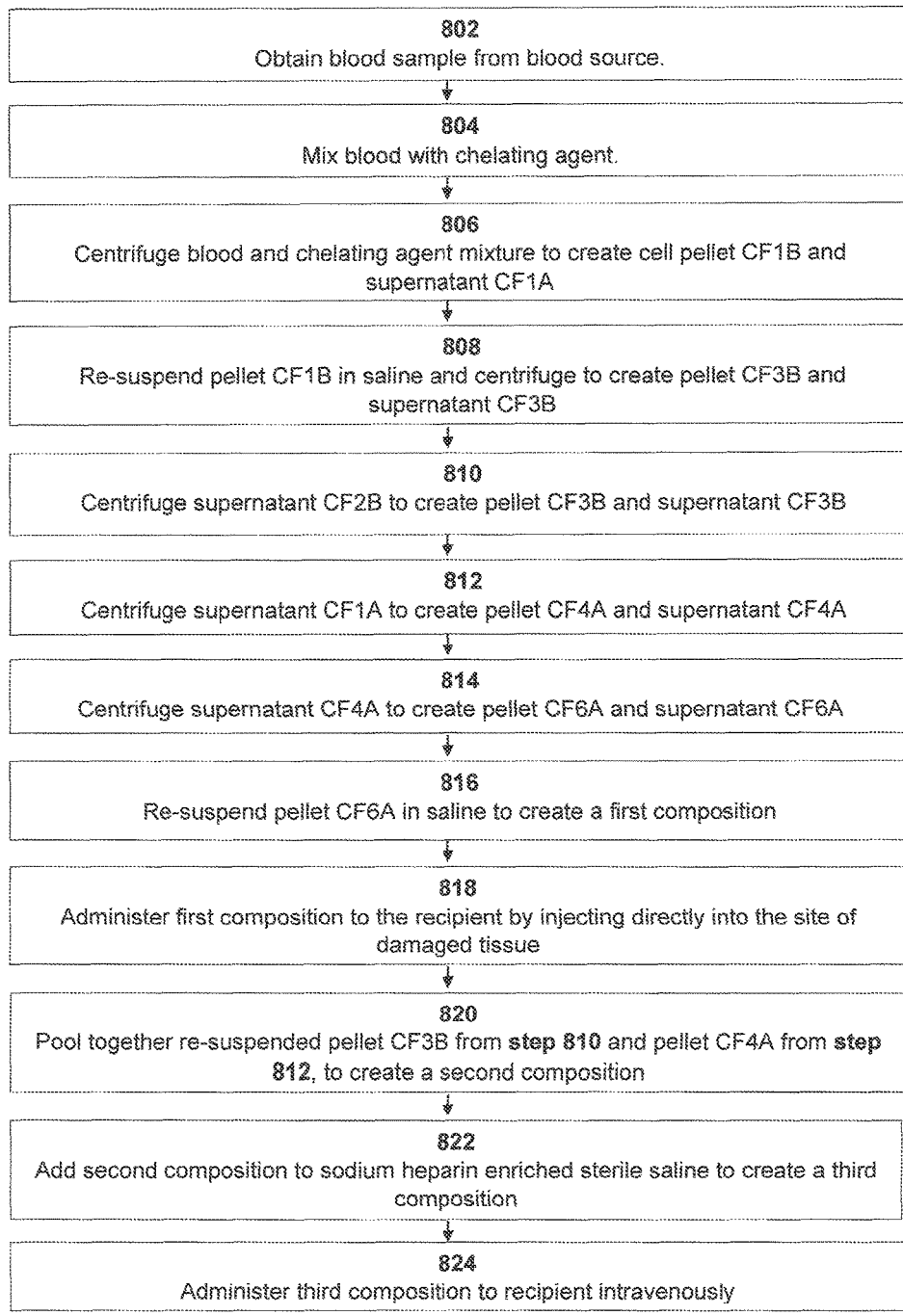
FIG. 4 illustrates a preferred embodiment of the invention wherein the damaged tissue to be treated is an internal organ or internal organ system and exposure to damaged tissue via intravenous administration is insufficient.

FIG. 4 illustrates a preferred embodiment of the invention wherein the damaged tissue to be treated is an internal organ or internal organ system, such as, by way of non-limiting example, cardiac, kidney, cardiovascular system, genitourinary system or joint tissue; and the MesoSCs and Nuc-P2s to be administered to the recipient are autologous, and exposure to damaged tissue via intravenous administration is insufficient. A blood sample is obtained from a blood source step 802. The blood sample is combined with a chelating agent, such as, EDTA (or EGTA blood-calcium chelator equivalent) to create a mixture step 804. The MesoSCs and Nuc-P2s in the blood-EDTA (or blood-EGTA or blood-calcium chelator equivalent) mixture are isolated by differential centrifugation to create pellet CF1B (containing MesoSCs$_{-10-12}$) and supernatant CF1A (containing Nuc-P2s$_{0.1-<10}$) step 806. This is accomplished by centrifuging the blood-EDTA (blood-EGTA or blood-calcium chelator equivalent) mixture between about 1 minute to about 10 minutes, preferably 8 minutes at a speed between about 200 RCF to about 20,000 RCF, preferably 3,500 RCF (see Table 1, CF1). The cell pellet CF1B contains the MesoSCs$_{10-12}$, as well as RBCs, WBCs, and platelets, whereas the supernatant CF1A contains the Nuc-P2s$_{0.1-<10}$. The MesoSCs are separated from the RBCs, WBCs, and platelets by re-suspending pellet CF1B in a 5 times pellet volume of about 0.1% to about 2% sterile saline, preferably 0.9% sterile saline and centrifuging for about 1 minute to about 10 minutes, preferably 5 minutes at about 200 RCF to about 20,000 RCF, preferably 300 RCF (see Table 1, CF2B), creating pellet CF2B (RBCs, WBCs, platelets) and supernatant CF2B (MesoSCs$_{10-12}$) step 808. The MesoSCs$_{10-12}$ are pelleted by centrifuging plasma supernatant CF2B for about 1 to about 10 minutes, preferably 5 minutes, at a speed of about 200 RCF to about 20,000 RCF, preferably 1,000 RCF (see Table 1, CF3B), to create pellet CF3B and supernatant CF3B, step 810. The Nuc-P2s$_{0.1-<10}$ in supernatant CF1A (from step 806 above) are further segregated into Nuc-P2s$_{0.1-<4}$ and Nuc-P2s$_{>4-<10}$. This is accomplished by centrifuging supernatant CF1A between about 1 minute to about 10 minutes, preferably 5 minutes at a speed between about 200 RCF to about 20,000 RCF, preferably 7,000 RCF, to create pellet CF4A (Nuc-P2s$_{>4-<10}$) and supernatant CF4A (Nuc-P2s$_{0.1-<4}$) (see Table 1, CF4A) step 812. The supernatant CF4A (Nuc-P2s$_{0.1-<4}$) is centrifuged about 1 minute to about 10 minutes, preferably 5 minutes at a speed between about 200 RCF to about 20,000 RCF preferably 13,000 RCF to create 2nd spin pellet CF4A and 2nd spin supernatant CF4A (see Table 1, CF4A 2nd spin) step 814.

FIG. 4 also illustrates a preferred embodiment of the invention wherein the damaged tissue to be treated is an internal organ or internal organ system, such as, by way of non-limiting example, cardiac, kidney, cardiovascular system, genitourinary system, or joint tissue; and the MesoSCs$_{10-12}$ and Nuc-P2s$_{0.1-<10}$ to be administered to the recipient are allogeneic, and exposure to damaged tissue via intravenous administration is insufficient. MesoSCs exhibit cell surface MHC-I and HLA-DR-II antigens whereby a competent immune system can recognize self (recipient) versus non-self (blood source) and elicit an immune response, if the cells are recognized as non-self. Therefore, if allogeneic MesoSCs are considered for transplant both the donor and the recipient need to be haplotyped to ascertain the compatibility of the allogeneic MesoSCs for transplant. If the haplotypes are either unknown or do not match, then the allogeneic donor MesoSCs are not utilized. In contrast, Nuc-P2s do not display either MHC-I and/or HLA-DR-II cell surface antigens. Therefore, allogeneic Nuc-P2s can be utilized for allogeneic donation. However, allogeneic plasma contains proteins, such as immunoglobulins, that can recognize self (blood source) from non-self (recipient) and must be removed prior to transplant to prevent an immune reaction culminating in a graft versus host disease. Therefore, whenever allogeneic haplotyped-matched MesoSCs and/or Nuc-P2s are utilized the donor allogeneic cells are washed extensively to remove plasma proteins that may adhere to the cells. A blood sample is obtained from a blood source step 802. The blood sample is combined with a chelating agent, such as, EDTA or EGTA to create a mixture step 804. The (optionally) haplotyped-matched MesoSCs$_{10-12}$ and Nuc-P2s$_{0.1-<10}$ in the blood-EDTA (or blood-EGTA or blood-calcium chelator equivalent) mixture are isolated by differential centrifugation to create pellet CF1B (containing optionally haplotyped-matched MesoSCs-$_{10-12}$) and supernatant CF1A (containing Nuc-P2s$_{0.1-<10}$) step 806. This is accomplished by centrifuging the blood-EDTA (blood-EGTA or blood-calcium chelator equivalent) mixture between about 1 minute to about 10 minutes, preferably 8 minutes at a speed between about 200 RCF to about 20,000 RCF, preferably 3,500 RCF (see Table 1, CF1). The cell pellet CF1B contains the optionally haplotyped-matched MesoSCs$_{10-12}$, as well as RBCs, WBCs, and platelets, whereas the supernatant CF1A contains the Nuc-P2s$_{0.1-<10}$. The (optionally) haplotyped-matched MesoSCs$_{10-12}$ are separated from the RBCs, WBCs, and platelets by re-suspending pellet CF1B in a 5 times pellet volume of about 0.1% to about 2% sterile saline, preferably 0.9% sterile saline and centrifuging for about 1 minute to about 10 minutes, preferably 5 minutes at about 200 RCF to about 20,000 RCF, preferably 300 RCF (see Table 1, CF2B), creating pellet CF2B (RBCs, WBCs, platelets) and supernatant CF2B (optionally haplotyped-matched MesoSCs$_{10-12}$) (see Table 1, CF2B) 808. The optionally haplotyped-matched MesoSCs$_{10-12}$ are pelleted by centrifuging plasma supernatant CF2B for about 1 to about 10 minutes, preferably 5 minutes, at a speed of about 200 RCF to about 20,000 RCF, preferably 1,000 RCF (see Table 1, CF3B), to create pellet CF3B and supernatant CF3B 810. The Nuc-P2s$_{0.1-<10}$ in supernatant CF1A (from step 806 above) are further segregated into Nuc-P2s$_{0.1-<4}$ and Nuc-P2s$_{>4-<10}$. This is accomplished by centrifuging supernatant CF1A between about 1 minute to about 10 minutes, preferably 5 minutes at a speed between about 200 RCF to about 20,000 RCF, preferably 7,000 RCF, to create pellet CF4A (Nuc-P2s$_{>4-<10}$) and supernatant CF4A (Nuc-P2s$_{0.1-<4}$) (see Table 1, CF4A) step 812. The supernatant CF4A (Nuc-P2s$_{0.1-<4}$) is centrifuged about 1 minute to about 10 minutes, preferably 5 minutes at a speed between about 200 RCF to about 20,000 RCF preferably 13,000 to create second spin pellet CF4A and second spin supernatant CF4A (see Table 1, CF4A second spin) step 814.

Autologous and/or allogeneic pellet CF4A (containing Nuc-P2s$_{0.1-<4}$) from step 814 above, is re-suspended in a clinically predetermined amount of about 0.01% to about 2% sterile saline with a preferred concentration of 0.9% sterile saline solution, creating a first composition step 816. This composition is injected directly at the site of the recipient's damaged tissue using an injecting device with or without fluoroscopic, ultrasound or other imaging guidance step 818.

Pellet CF3B from step 810 above, (containing autologous and/or optionally haplotyped-matched MesoSCs$_{10-12}$) and pellet CF4A from step 812 above (containing autologous and/or allogeneic Nuc-P2s$_{>4-<10}$) are re-suspended and combined in a volume of about 0.01% to about 2% sterile saline, with a preferred concentration of 0.9% sterile saline to create a second composition step 820. The second composition is then added to a clinically determined volume of about 0.01% to about 2% sterile saline (enriched with sodium heparin) to create a third composition step 822. The enriching sodium heparin having a concentration range of about 1 to about 10,000 units of heparin with a preferred concentration of 12 units per Kg bodyweight up to a maximum of 1,000 units heparin per about 1 to about 2,000 ml of sterile saline with a preferred volume of 500-ml of sterile saline. The third composition, in 0.9% sterile saline and sodium heparin has a preferred concentration of 1,000 units heparin per about 1 to about 2,000-ml of sterile saline, preferably a volume of 500-ml, and is administered to the recipient intravenously at a slow drip rate step 824. The drip rate being about 100-ml to about 1000-ml per hour and at a preferred drip rate of 500-ml per hour. It may be necessary to modify total volume and preferred time of infusion in patients with cardiovascular or renal conditions. The sodium heparin prevents clot formation during administration of the composition. The tissues outside the vasculature contain collagens and extracellular matrix macromolecules that function to aid in the attachment of the autologous and/or (optionally) haplotyped-matched allogeneic $MesoSCs_{10-12}$ and autologous and/or allogeneic $Nuc-P2s_{>4-<10}$ to other damaged tissues within the body. The additional wash steps of the allogeneic $MesoSCs_{10-12}$ and $Nuc-P2s_{>4-<10}$ with 0.9% sterile saline removes allogeneic plasma proteins such as immunoglobulins, thereby reducing the likelihood of rejection of the (optionally) haplotyped-matched allogeneic $MesoSCs_{10-12}$ and allogeneic $Nuc-P2s_{>4-<10}$ by the recipient's immune system. The sterile saline also provides a medium for introducing the MesoSCs and $Nuc-P2s_{>4-<10}$ and assists in replacing fluid loss from obtaining the blood samples. The slow intravenous administration allows the autologous and/or (optionally) haplotyped-matched allogeneic $MesoSCs_{10-12}$ and autologous and/or allogeneic $Nuc-P2s_{>4-<10}$ maximal time for their exposure to damaged tissue sites. This separate administration of the autologous and/or optionally haplotyped-matched allogeneic $MesoSCs_{10-12}$ and autologous and/or allogeneic $Nuc-P2s_{>4-<10}$ to the recipient intravenously reduces the likelihood of the recipient's body from diverting the site-directed autologous and/or allogeneic $Nuc-P2s_{0.1-<4}$ for use in other parts of the body by making the autologous and/or (optionally) haplotyped-matched allogeneic $MesoSCs_{10-12}$ and autologous and/or allogeneic $Nuc-P2s_{>4-<10}$ available for that purpose. As a benefit of this method, the maximum number of injected autologous and/or allogeneic $Nuc-P2s_{0.1-<4}$ are available for tissue repair at the specific directed site.

In a non-limiting example showing one embodiment of the invention is as follows:

Prior to Procedure:

At least one month, preferably longer, the recipient begins taking a Nuc-P2 stimulator such as ingesting an antioxidant and/or flavonoid, such as, by way of a non-limiting example, ½-1 cup of fresh or frozen/thawed blueberries or powdered blueberry equivalent daily per one hundred to two hundred pound individual.

At least one month prior to procedure recipient abstains from alcohol and minimizes caffeine intake. The preferred amount of caffeine is none, but one can ingest up to 8 oz coffee/tea/soda-containing caffeine per day maximum.

Nuc-P2 Procedure:

Day 1, the recipient travels to location for the MesoSC/Nuc-P2 procedure and, checks into accommodations (if necessary), and rests for the remainder of the day.

Day 2, the recipient rests or is limited to minimal activity for at least 24 hours prior to the MesoSC/Nuc-P2 procedure. The recipient checks into the clinic. The MesoSC/Nuc-P2 procedure is described to the recipient, stressing risks and benefits and the recipient signs a medical waiver for procedure. A history and physical are performed to determine whether there are any contraindications for the procedure. Absolute contraindications for the procedure include active cancer or cancer treatment. The relative contraindications for the procedure include, but are not limited to the following: a history of cancer remission within the last two to five years, uncontrolled congestive heart failure or other causes of unstable cardiovascular status, uncontrolled renal disease contributing to unstable cardiovascular status, poorly controlled hemophilia or disorders of coagulation leading to hypercoagulable state (increased blood-clotting). If the recipient is predisposed to a hypercoagulable state, they can be pre-injected with heparin prior to drawing a blood sample if the recipient is not allergic to heparin. The recipient is asked to confirm that he or she has no history of active neoplasms and their cardiovascular and renal status are assessed for potential contraindications. The recipient is asked whether he or she has a coagulation (blood clotting) problem. The recipient is given a mobilizing agent, such as, by way of a non-limiting example, 2×500 mg capsules of AFA (Aphanizomenon flos-aquae) per one hundred to two hundred pound individual as a Nuc-P2 mobilizer and told to take it as directed (approximately 18 hours before blood draw for Nuc-P2 and MesoSC harvest).

Approximately 18 hours before actual blood is drawn, the recipient undertakes a mobilizing activity or ingests a Nuc-P2 mobilizer, by way of a non-limiting example, such as 2×500 mg capsules of AFA (Aphanizomenon flos-aquae).

Day 3, is the MesoSC/Nuc-P2 procedure day where the procedure is again described to the recipient, stressing risks and benefits. The recipient, (and/or the recipient's legal guardian or medical power of attorney) signs a second medical waiver for the procedure.

The recipient's vital signs are re-taken, including the recipient's weight. The recipient is asked whether he or she has a blood clotting problem. If the recipient does have a blood clotting disorder the recipient can be pre-injected with heparin, if medically appropriate, prior to drawing the blood sample if the recipient is not allergic to heparin. The recipient is asked to confirm that he or she has no history of active neoplasms or active cancer treatment. Individuals having active cancer or active cancer treatment are excluded as candidates for this treatment method, as a history of active cancer or active cancer treatment is clinically contraindicated.

The maximal amount of blood that can be withdrawn from a human blood source is calculated based on blood source's body weight, using standard Red Cross guidelines for blood donation.

The blood source's skin area for blood draw is swabbed with alcohol or other aseptic agent and allowed to air dry.

If it is determined that the blood source is at risk for increased clotting innately, or as a result of the procedure, then prophylactic heparin may be given to the blood source or recipient, at about 40 units of heparin per Kg body weight up to about 4,000 units as an IV bolus followed by about 12 units per Kg per hr up to a maximum of about 1,000 units. It should be understood that it is not necessary to allow the blood source to continue receiving heparin after the initial blood draw is complete. If the blood source is not deemed to clot excessively, a bolus of about 40 units per Kg body weight is injected. If the blood source has a tendency to bleed excessively, then heparin is not given.

The blood sample range of about 1 ml to about 500 ml, with a preferred range of about 50 to about 400 ml, is withdrawn into a first set of containers, such as EDTAhemaovac tubes (5-40 tubes, depending on procedure to be performed) or syringes preloaded with EDTA (or EGTA or calcium chelator equivalent).

Each of the first set of containers after the blood collection, is pulse vortexed (at a setting between about 1 to about 10 with a preferred setting of 6-8) three times and allowed to sit on wet ice until all of the first set of containers are collected. If syringes are utilized for blood collection, they are inverted 3-5 times and placed on wet ice, then transferred to the first set of containers. Blood from either the first set of containers or syringes are transferred to centrifugation containers.

The centrifugation containers are refrigerated for a minimum of two hours. The centrifugation containers are then placed into a centrifuge and spun between about 1 minute and about 10 minutes, preferably 8 minutes, at a temperature between about 2 to about 8 degrees Centigrade, preferably 4 degrees Centigrade, at a speed between about 200 RCF and about 20,000 RCF, preferably 3,500 RCF resulting in a cell pellet CF1B and a supernatant CF1A (see FIG. 1, CF1). The above centrifugation may also be performed in a refrigerated centrifuge, and may be included as part of the refrigeration processing time.

The supernatant CF1A plasma is removed from each container in the first set of containers leaving the hematopoietic elements (red blood cells, white blood cells, platelets) and MesoSCs behind and the plasma supernatant CF1A is pooled into a second set of centrifugation containers.

The hematopoietic elements/MesoSCs can be further processed for MesoSCs and/or platelet rich plasma (PRP) or discarded. If PRP is wanted (see paragraph below). However, if PRP, MesoSCs and/or Nuc-P2s are given at same time, the inductive factors within the PRP will induce the MesoSCs and Nuc-P2s to form a connective tissue scar at site of injection.

If MesoSCs are wanted, the pellet CF1B is processed as follows. The pellet(s) are refrigerated for a minimum of two hours at about 2 to 8 degrees Centigrade, preferably 4 degrees Centigrade. The mesodermal stem cells are separated from the RBCs, WBCs, and platelets by re-suspending the cell pellet CF1B in a 5 times pellet volume of about 0.1% to about 2% sterile saline, preferably 0.9% sterile saline and centrifuging for about 1 minute to about 10 minutes, preferably 5 minutes at about 200 RCF to about 20,000 RCF, preferably 500 RCF (see FIG. 1; Table 1 CF2B), resulting in pellet CF2B (RBCs, WBCs, platelets) and saline-supernatant CF2B (MesoSCs$_{10\text{-}12}$). MesoSCs can be pelleted by centrifuging saline-supernatant CF2B for about 1 minute to about 10 minutes, preferably 5 minutes, at a speed of about 200 RCF to about 20,000 RCF, preferably 1,000 RCF (see FIG. 1; Table 1, CF3B), resulting in pellet CF3B and supernatant CF3B. The above centrifugation may also be performed in a refrigerated centrifuge, and may be included as part of the refrigeration processing time.

If PRP is wanted, the hematopoietic elements are re-suspended in equal volume of sterile saline with heparin. Re-suspended hematopoietic elements are processed following standard PRP procedures commonly known to one skilled in the art.

The second set of centrifugation containers containing the pooled plasma supernatant from CF1 (see FIG. 1; Table 1, CF2A) are refrigerated for at least two hours at about 2 to 8 degrees Centigrade, preferably 4 degrees Centigrade. The containers are then placed into a centrifuge, and spun for about 1 minute to about 10 minutes, preferably for 5 min at about 200 RCF to about 20,000 RCF, preferably 8,000 RCF and 13,000 RCF for central nervous system repair (see FIG. 2a; Table 1, first spin pellet, CF5A and CF6A); at 4,500 and 13,000 RFC for respiratory system repair (see FIG. 2a; Table 1, CF2A—first and second spin pellet); at 10,000 RCF for cardiac, kidney, other internal organ, internal organ system, or joint repair (see FIG. 2b; Table 1, CF1, second spin pellet); or at 6,000 and 10,000 RCF for direct injection (see Table 1; FIG. 2a; Table 1, CF3A—first and second spin pellets). The above centrifugation may also be performed in a refrigerated centrifuge, and may be included as part of the refrigeration processing time.

The plasma supernatant is removed from each tube of the second set of centrifugation containers leaving the pelleted material behind and pooled into a third set of containers. The pelleted material from the second set of containers is stored on wet ice or under refrigeration for further processing:

The third set of containers are refrigerated for a minimum of two hours total time of processing at about 2 to 8 degrees Centigrade, preferably 4 degrees Centigrade. The containers are then placed into a centrifuge and spun for about 1 minute to about 10 minutes, preferably for 5 min, at about 200 RCF to about 20,000 RCF, preferably at 13,000 RCF for central nervous system repair (see Table 1, CF6A); respiratory system repair, cardiac repair, kidney repair, other internal organ or internal organ system repair with systemic infusion (see Table 1, CF1—2nd spin pellet), or introduction by site-directed injection (see Table 1, CF4A). The above centrifugation may also be performed in a refrigerated centrifuge, and may be included as part of the refrigeration processing time.

The 2nd spin supernatants from each container of the third set of containers is removed and discarded leaving the cell pellet behind for further processing.

The Nuc-P2 pellets from the second set of containers are re-suspended by vortexing in a small volume of sterile saline, by way of non-limiting example, 1 to 10 Nuc-P2 pellet volumes, preferably 2 pellet volumes, pooled, and vortexed.

The re-suspended and pooled Nuc-P2 pellets from the second set of containers are refrigerated for a minimum of two hours total time of processing at about 2 to 8 degrees Centigrade, preferably 4 degrees Centigrade. The re-suspended and pooled Nuc-P2 pellets from the second set of containers are then centrifuged for about 1 to about 10 minutes, preferably 5 min, at about 200 RCF to about 20,000 RCF, preferably 13,000 RCF for central nervous system (see Table 1, CF6A); respiratory system, internal organs, internal organ systems (see Table 1, CF1—2nd spin pellet); and for site-directed injection (see Table 1, CF4A). The above centrifugation may also be performed in a refrigerated centrifuge, and may be included as part of the refrigeration processing time.

The Nuc-P2 pellets from the spin of the third set of containers are re-suspended by vortexing in a small volume of sterile saline, such as, by way of non-limiting example, about 1 to about 10 Nuc-P2 pellet volumes, preferably 2 Nuc-P2 pellet volumes, pooled and vortexed.

The re-suspended and pooled Nuc-P2 pellets from the third set of containers are refrigerated for a minimum of two hours total time of processing at about 2 to 8 degrees Centigrade, preferably 4 degrees Centigrade. The re-suspended and pooled Nuc-P2 pellets from the third set of containers are centrifuged for about 1 minute to about 10 minutes, preferably 5 min, at about 200 RCF to about 20,000 RCF, preferably 13,000 RCF for central nervous system repair (see Table 1, CF6A); respiratory system repair, or internal organ or internal organ system repair (see Table 1, CF1—2nd spin pellets); and for introduction by site-directed injection (see Table 1, CF4A). The above centrifugation may also be performed in a refrigerated centrifuge, and may be included as part of the refrigeration processing time.

Example 1

For central nervous system treatments, such as, by way of non-limiting example, the brain, the recipient is requested to clean out nasal mucus utilizing 0.65% nasal saline.

The activated Nuc-P2s$_{0.1-2}$ from the second spin (Table 1, CF5A) are loaded into a topical applicator, by way of a non-limiting example, such as 1 cc tuberculin syringe barrels and given by intranasal topical application.

Example 2

For treatments of the respiratory system, such as, by way of non-limiting example, the lung: The activated Nuc-P2s$_{0.1-8}$ from the second spin (see Table 1, CF2A—2nd spin pellet) are diluted to 5-ml total volume with sterile saline, divided into two halves (of 2.5 ml each) and one half (2.5 ml) is nebulized.

Example 3

For systemic treatments of internal organs, or organ systems such as, by way of non-limiting example, cardiovascular, gastrointestinal, genitourinary, endocrine, autoimmune system: Activated MesoSCs and Nuc-P2s from the first spin (see Table 1, CF1—2nd pellet spin, CF3B—first pellet spin) are placed within a 500-ml bag of sterile saline and given by IV infusion. Heparin is added to the IV infusion bag, prior to the activated MesoSCs and Nuc-P2s, at a dosage of about 12 units per Kg bodyweight with a maximum of about 1,000 units. The re-suspended MesoSCs and Nuc-P2s are injected into a range of about 100-ml to about 2,000-ml of sterile saline, with a preferable quantity of 500-ml and infused over about 30 to about 60 minutes. The drip rate being about 100-ml to about 1000-ml per hour at a preferred drip rate of 500-ml per hour. It may be necessary to modify total volume and preferred time of infusion in patients with cardiovascular or renal conditions. If the recipient bleeds excessively, no heparin is added to the Nuc-P2/saline composition.

Example 4: For Direct Injection with or without Fluoroscopic, Ultrasound, or Other Imaging Guidance About 1 to about 1000 microliters of Nuc-P2$_{0-1-<4}$ of the re-suspended second spin pellet with a preferred volume of 50 microliters from the 13,000 RCF second spin is added to a microcentrifuge tube.

About 1 to about 1000 microliters of Trypan blue with a preferred volume of 50 microliters is added to the microcentrifuge tube.

The contents of the microcentrifuge tube are triturated about 1 to about 20 times with a preferred repetition of 10 times with a micropipettor. Alternatively, the 100 microliter sample is counted on a hemocytometer, flow cytometer, fluorescent activated cell sorter, or automated cell counter.

The 100 microliters of Trypan blue-stained Nuc-P2s$_{0.1-<4}$ re-suspended second spin pellet suspension is placed onto a hemocytometer and viewed under a microscope. Alternatively, the 100 microliter sample is counted on a flow cytometer.

The number of Nuc-P2s$_{0.1-<4}$ per 1 cc (cubic centimeter) volume is calculated and loaded into an injecting device, such as, by way of non-limiting example, a syringe or syringes for needle insertion, with or without fluoroscopic, ultrasound, or other imaging guidance. The dose of Nuc-P2s$_{0.1-<4}$ at the injection site is in a range of about 1 million to about 10 trillion Nuc-P2s$_{0.1-<4}$, with a preferable effective dose at injection site of approximately 1 million Nuc-P2s$_{0.1-<4}$ per 1 cubic centimeter (cc) tissue to be repaired.

For Systemic IV Infusion of MesoSCs and Nuc-P2s, all Procedures:

The pellets from the first spins, such as, CF3B (MesoSCs$_{10-12}$) and either CF2A (Nuc-P2s$_{>8<10}$), CF3A (Nuc-P2s$_{6->10}$), CF4A (Nuc-P2s$_{>4->10}$), and/or CF5A (Nuc-P2s$_{>2-<10}$) (Table 1), are re-suspended using about 0.01% to about 2.0%, preferably 0.9% sterile saline and vortexed. Heparin is first added to the IV infusion bag at a dosage of about 12 units per Kg bodyweight with a maximum of 1,000 units. Then the re-suspended Nuc-P2s are injected into the IV infusion bag at a range of about 1-ml to about 2000-ml of sterile saline, with a preferable quantity of 500-ml and infused over about 30 to about 60 minutes. The drip rate being about 100-ml to about 1000-ml per hour at a preferred drip rate of 500-ml per hour. It may be necessary to modify total volume and preferred time of infusion in patients with cardiovascular or renal conditions. If the recipient bleeds excessively, no heparin is added to the MesoSCs/Nuc-P2s/saline composition for IV infusion.

Post MesoSC/Nuc-P2 Treatment, all Procedures

Day 3—The recipient rests the remainder of day 3 with minimal activity.

Day 4—The recipient rests with minimal activity and may travel home.

Day 5—The recipient rests, but can pursue light activities and may travel home.

The first month post MesoSC/Nuc-P2 procedure the recipient abstains from alcohol and minimizes caffeine intake. It is preferable that the recipient has no caffeine intake but can ingest up to 8 oz coffee/tea/soda-containing caffeine per day maximum.

The second month post MesoSC/Nuc-P2 procedure the recipient limits alcohol intake to equivalence of 1-2 glasses of wine per day and caffeine intake to 16 oz coffee/tea/soda per day, maximum.

The third month and forward, the recipient can resume his or her normal schedule.

Figure 5:
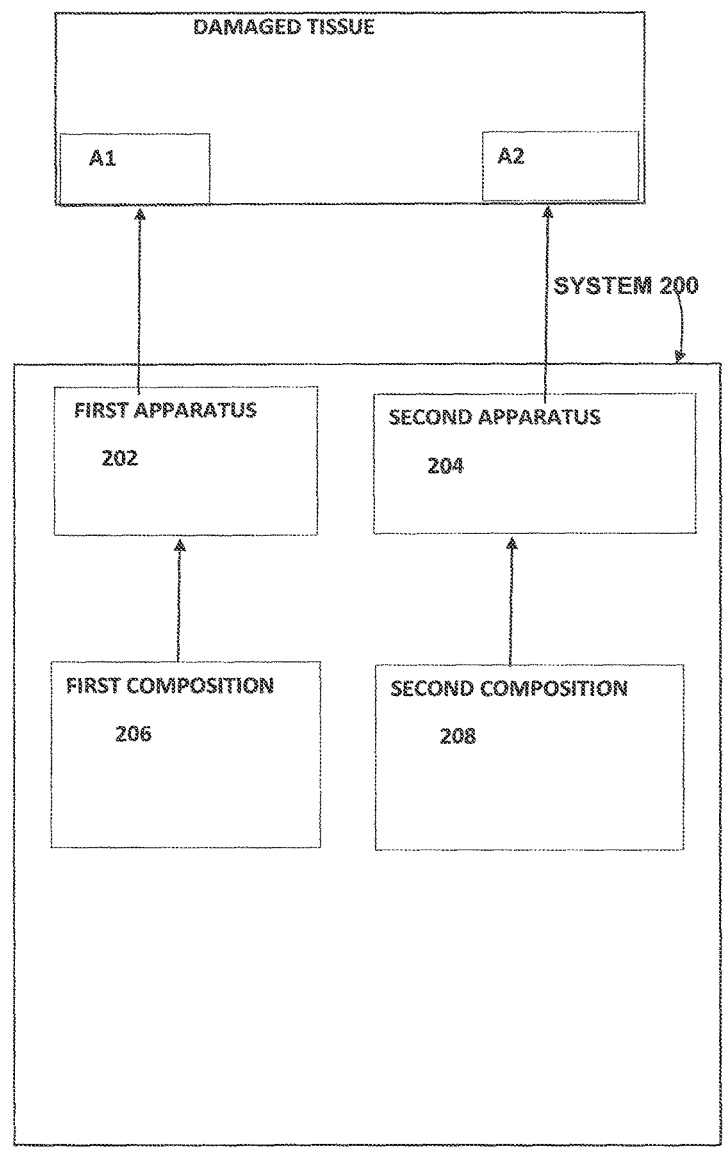
FIG. 5 is an illustration of the system for treating damaged tissue with optimally isolated Nuc-P2s and MesoScs.

Referring to FIG. 5, another preferred embodiment of the invention is a system 200 for the treatment of damaged tissue targets with optimally isolated adult derived MesoSCs and Nuc-P2s. As shown, the system, 200, comprises a first composition, 206, and a second composition, 208, and a first apparatus and a second apparatus, 202, 204 respectively, for placing the first composition, 206, and the second composition, 208, into one or more damaged tissue target areas A1, A2. The first composition, 206, comprises one or more of the following: MesoSCs, Nuc-P2s and sterile saline. It should be understood that the specific contents of the first composition is dependent upon the tissue being treated and the location of the tissue being treated as described above. In another preferred embodiment, the second composition, 208 comprises one or more of the following: MesoSCs Nuc-P2s, sterile saline and sodium heparin. It should be understood that the specific contents of the second composition, 208, is dependent upon the tissue being treated and the location of the tissue being treated as described above. As shown, the first apparatus, 202, operates to introduce the first composition, 206, to one or more damaged tissue targets A1. It should be understood that the first apparatus, 202, for introducing the first composition, 206, into a tissue target depends upon the tissue being treated and the location of the tissue being treated as described above. As shown, the second apparatus, 204, operates to introduce the second composition, 208, to one or more damaged tissue targets A2. It should be understood the second apparatus, 204, for introducing the second composition, 208, is dependent upon the tissue being treated and the location of the tissue being treated as described above. In a preferred embodiment, the first apparatus, 202, for introduction of the first composition, 206, into the damaged tissue, A1, includes by way of a non-limiting example, one or more of the following: direct injection with or without fluoroscopic, ultrasound, or other imaging guidance, nebulization, or intravenous drip. In another preferred embodiment, the second apparatus, 204, for introduction of the second composition, 208, includes, by way of a non-limiting example intravenous drip.

Those of ordinary skill in the art will realize that variations of isolation techniques can be utilized based on the inherent properties of the MesoSCs and Nuc-P2s. The MesoSCs and Nuc-P2 properties include charge, size, density, cell surface epitopes, and viability post mortem. These properties can be used for isolation of MesoSCs and Nuc-P2s for subsequent immediate use or for propagation ex vivo prior to use. These isolation techniques may include, but are not limited to, electrophoretic mobility based on charge and size, gravity sedimentation post mortem, antibodies based on cell surface epitopes, filtration based on size, refrigeration, and centrifugation based on size, and density. One of ordinary skill in the art would also realize that speeds up to 20,000 RCF can be utilized to isolate viable MesoSCs and Nuc-P2s and times up to thirty plus days can be utilized based on their viability after removal from their respective host/blood source.

By way of another non-limiting example, another preferred embodiment of the method for optimizing the isolation of Mesodermal Stem Cells (MesoSCs) and Nucleated Plasma Particles (Nuc-P2s) for repair of damaged tissue comprising the steps of: stimulating the proliferation of MesoSCs and Nuc-P2s in a blood source by administering a predetermined dose of one or more stimulators to the blood source; inducing the migration of the proliferated MesoSCs and Nuc-P2s into the circulatory system in the blood source by administering a predetermined dose of one or more mobilizers; administering a predetermined dose of anticoagulant to the blood source; obtaining a blood sample from the blood source; administrating a divalent cation chelator to the blood sample to restore MesoSCs and Nuc-P2s' zeta potential; refrigerating the blood sample to restore active binding sites; separating MesoSCs and Nuc-P2s from the blood sample; and further separating MesoSCs and subtypes of Nuc-P2s based upon the damaged tissue type and repair desired wherein the blood source is a mammal or non-mammal. The method wherein one or more of the stimulators are antioxidants and/or flavonoids. The method wherein the antioxidants are selected from the group consisting essentially of fresh or frozen or powdered blueberries, raspberries, blackberries and concord grapes. The method wherein one or more of the mobilizers are selected from the group consisting of a Cyanobacter (Aphanizomenon flos-aquae, AFA), chorella, exercise, and physical trauma. The method of wherein the divalent cation chelator is selected from the list consisting of, Ethylenediaminetetraacetic acid (EDTA), Ethyleneglycol bis (2-Aminoethyl ether)-N,N,N',N' tetraacetic acid (EGTA), or a calcium chelator equivalent. The method for treating damaged tissue with optimally isolated Mesodermal Stem Cells (MesoSCs) and Nucleated Plasma Particles (Nuc-P2s) comprising the steps of: identifying a recipient having damaged tissue to be treated; identifying the tissue type to be treated; determining a route for introduction of MesoSCs and specific Nuc-P2 sub-types to the damaged tissue; introducing MesoSCs and specific Nuc-P2 sub-types to the damaged tissue; introducing MesoSCs and Nuc-P2 sub-types to the recipient systemically. In a preferred embodiment, the optimal isolation of MesoScs and Nuc-P2s is performed by differential centrifugation. In a preferred embodiment, the route of introduction of specific. Nuc-P2 sub-types is performed by topical application. In another preferred embodiment, the route of introduction of specific Nuc-P2 sub-types is performed by nebulization. In another preferred embodiment, the route of introduction of specific Nuc-P2 sub-types is performed by direct needle injection with or without fluoroscopic, ultrasound, or other imaging guidance. In another preferred embodiment, the route of introduction of specific Nuc-P2 sub-types is performed by intravenous drip. In another preferred embodiment, the route of introduction of specific Nuc-P2 sub-types is performed by the method wherein the route of introduction of specific Nuc-P2 sub-types and MesoSCs is accomplished by intravenous drip.

By way of another non-limiting example, another preferred embodiment of the invention is a system for treating damaged tissue in a subject with optimally isolated adult derived MesoSCs and Nuc-P2s, the system comprising: a first apparatus; a first composition contained in the first apparatus, wherein the first apparatus is selected from the group comprising, an intravenous drip, hypodermic needle, topical applicator and nebulizer; a second apparatus; a second composition contained in the second apparatus wherein the second apparatus is an intravenous drip, wherein the first composition consists essentially of primary treating stem cells and sterile saline, and wherein the second composition consists essentially of secondary treating stem cells, sterile saline and sodium heparin. Preferably, the first system operates to deliver a first composition to a first target area in the recipient and a second apparatus operates to deliver a second composition to a second target area in the recipient. In another preferred embodiment, the first target area and the second target area are at the same location in the subject.

In another preferred embodiment, the first target area is a central nervous system and the primary treating stem cells are Nuc-P2s having a size from about 0.1 microns to about 2.0 microns and wherein the second target area is a circulatory system or an internal organ or an internal organ system and wherein the secondary treating stem cells are Nuc-P2s having a size between greater than about 2.0 microns to less than about 10 microns and MesoSCs having a size between greater than 10 microns to less than about 12 microns. In another preferred embodiment, the first target area is a respiratory system and the primary treating stem cells are Nuc-P2s having a size from about 0.1 to about 8.0 microns and wherein the second target area is a circulatory system or an internal organ or an internal organ system and wherein the secondary treating stem cells are Nuc-P2s having a size between greater than about 8 microns to less than about 10 microns and MesoSCs having a size between greater than 10 microns to less than about 12 microns.

In another preferred embodiment, the first target area is an internal organ, an internal organ system, circulatory system, or joint, and the first delivery apparatus is an injecting device and the primary treating stem cells are Nuc-P2s having a size from about 0.1 microns to less than about 4.0 microns and the second target area is a circulatory system or an internal organ and the secondary treating stem cells are Nuc-P2s having a size between about 4.0 microns to less than 10 microns. In another preferred embodiment the first target area and said second target area is a circulatory system or an internal organ or internal organ system and the first delivery apparatus and the second delivery apparatus is an intravenous drip and the primary treating stem cells are Nuc-P2s having a size from about 0.1 microns to less than about 4.0 microns and the secondary treating stem cells are Nuc-P2s having a size from about 4.0 microns to less than about 10 microns and MesoSCs having a size between greater than 10 microns to less than about 12 microns.

Although this invention has been primarily described in terms of specific examples and embodiments thereof, it is evident that the foregoing description will suggest many alternatives, modifications, and variations to those of ordinary skill in the art. Accordingly, the appended claims are intended to embrace, as being within the spirit and scope of invention, all such alternatives, modifications, and variations.

The invention claimed is:

1. A system for treating damaged tissue in a subject with optimally isolated adult derived MesoSCs and Nuc-P2s the system comprising:
a first apparatus effective for attaching to a first target area in the subject;
a first composition contained in said first apparatus, wherein said first apparatus is selected from the group comprising, an intravenous drip, injecting device, topical applicator and nebulizer;
a second apparatus effective for attaching to a second target area in the subject;
a second composition contained in said second apparatus wherein said second apparatus is an intravenous drip;
wherein said first composition is effective for treating damaged tissue in said first target area and consists essentially of primary treating stem cells and sterile saline, and wherein said second composition consists essentially of secondary treating stem cells, sterile saline and sodium heparin;
wherein said second composition is effective for preventing the body from diverting primary treating stem cells from said first target area.

2. The system of claim 1 wherein said first apparatus operates to deliver said first composition to said first target area in the recipient and said second apparatus operates to deliver said second composition to said second target area in the recipient.

3. The system of claim 1 wherein said first target area is a central nervous system and said primary treating stem cells are Nuc-P2s having a size from about 0.1 microns to about 2.0 microns and wherein said second target area is a circulatory system or an internal organ or internal organ system and wherein said secondary treating stem cells are Nuc-P2s having a size between greater than about 2.0 microns to less than about 10 microns and MesoSCs having a size between greater than 10 microns to less than about 12 microns.

4. The system of claim 1 wherein said first target area is a respiratory system and said primary treating stem cells are Nuc-P2s having a size from about 0.1 to about 8.0 microns and wherein said second target area is a circulatory system or an internal organ or internal organ system and wherein said secondary treating stem cells are Nuc-P2s having a size between greater than about 8 microns to less than about 10 microns and MesoSCs having a size between greater than 10 microns to less than about 12 microns.

5. The system of claim 1 wherein said first target area is an internal organ, an internal organ system, circulatory system, or joint, and said first apparatus is an injecting device and said primary treating stem cells are Nuc-P2s having a size from about 0.1 microns to less than about 4.0 microns and said second target area is a circulatory system or an internal organ or internal organ system and said secondary treating stem cells are Nuc-P2s having a size between about 4.0 microns to less than 10 microns and MesoSCs having a size between greater than 10 microns to less than about 12 microns.

6. The system of claim 1 wherein said first target area and said second target area is a circulatory system or an internal organ or internal organ system and said first apparatus and said second apparatus is an intravenous drip and said primary treating stem cells are Nuc-P2s having a size from about 0.1 microns to less than about 4.0 microns and said secondary treating stem cells are Nuc-P2s having a size from about 4.0 microns to less than about 10 microns and MesoSCs having a size between greater than 10 microns to less than about 12 microns.

* * * * *